(12) United States Patent
Fu

(10) Patent No.: US 7,076,371 B2
(45) Date of Patent: Jul. 11, 2006

(54) NON-INVASIVE DIAGNOSTIC AND MONITORING METHOD AND APPARATUS BASED ON ODOR DETECTION

(76) Inventor: Chi Yung Fu, 1005 Duncan St., San Francisco, CA (US) 94131

( * ) Notice: Subject to any disclaimer, the term of this patent is extended or adjusted under 35 U.S.C. 154(b) by 239 days.

(21) Appl. No.: 10/087,049

(22) Filed: Mar. 2, 2002

(65) Prior Publication Data

US 2003/0008407 A1 Jan. 9, 2003

Related U.S. Application Data

(60) Provisional application No. 60/273,125, filed on Mar. 3, 2001.

(51) Int. Cl.
*G01N 33/48* (2006.01)
*G06F 19/00* (2006.01)
*G06G 7/58* (2006.01)

(52) U.S. Cl. .............................. 702/19; 702/24; 703/11

(58) Field of Classification Search .................. 702/19, 702/22, 27; 436/1
See application file for complete search history.

(56) References Cited

U.S. PATENT DOCUMENTS 5,664,066 A * 9/1997 Sun et al. ...................... 706/25
6,170,318 B1 * 1/2001 Lewis ........................ 73/23.34
6,221,026 B1 * 4/2001 Phillips ....................... 600/532

OTHER PUBLICATIONS

Gardner et al., Br. J. Ophthalmol., vol. 80, pp. 937-938, 1996.*
Matteucci et al., Diabetes Care, vol. 23, pp. 1182-1186, 2000.*
Kanety et al., PNAS, vol. 91, pp. 1853-1857, 1994.*
Brook et al., Journal of Clinical Microbiology, vol. 33, pp. 2382-2387, 1995.*
Pavlou et al., Biosensors & Bioelectronics, vol. 15, pp. 333-342, 2000.*
Acetone, Dictionary.com Website, p. 1, 2004.*
Ping et al. (1997) A novel method for diabetes diagnosis based on electronic nose. Biosensors & Bioelectronics vol. 12, pp. 1031-1036 (1997).*
Ping et al. (1996) A novel method combined neural network with fuzzy logic for odour recognition. Meas. Sci. Technol. vol. 7, pp. 1707-1712 (1996).*

* cited by examiner

*Primary Examiner*—John S. Brusca

(57) ABSTRACT

A set of volatile markers are determined which are characteristic of a particular condition or disease, and which will be found in the exhaled breath of a person or odor from other parts of a body or from an entity. These markers are detected in the breath odor or gaseous emanations from the body or entity noninvasively using a volatile substance detector of sufficient sensitivity, such as an artificial olfactory system. The detected marker data is processed in an artificial neural network/fuzzy filter system with an algorithm that intelligently adapts to the individual body or entity and also optionally (if necessary) with a correction algorithm to eliminate environmental and other erroneous contributions to the markers. Any number of markers may be used, depending on how well they correlate with the condition and how accurate a result is desired, i.e. general screening or accurate diagnosis and monitoring.

29 Claims, 12 Drawing Sheets

NON-INVASIVE DIAGNOSTIC AND MONITORING METHOD AND APPARATUS BASED ON ODOR DETECTION

RELATED APPLICATIONS

Applicant claims priority from provisional application Ser. No. 60/273,125 filed Mar. 3, 2001.

BACKGROUND OF THE INVENTION

The invention relates to odor or chemical or biological sensors, and more particularly to sensors for detecting or monitoring chemical or biochemical conditions, including those related to diseases.

Almost any entity can be defined by its chemical (chemical, electrochemical or biochemical) state. The identification of such a state can be inferred or diagnosed by various markers that characterize the state. Changes in the values of the markers or changes in the applicable markers represent a transition from one state to another. This applies to be both living and non-living entities or systems.

For example, the toxic leak of an electrical transformer is possibly characterized by the presence of PCB fluid outside the transformer. In this case, the leaking state is marked by the external presence of the PCB marker. The well-being of a human, which is on the other extreme of complexity, could also be defined by his/her chemical or more precisely by his/her biochemical state with its corresponding markers. When a particular disease, illness or injury occurs and progresses, the presence of particular markers and their values for each disease would represent the status and the progression of the condition. Thus monitoring of the markers corresponding to the disease is essential for medical diagnosis and treatment.

For traditional medical diagnosis, blood and urine and the two most common media for obtaining these markers for evaluation. However, a medium that has been largely neglected by the medical community is expired gases or odors from one's breath or from other parts of the body. Such a technique offers the potential of totally non-invasive evaluation and investigation, a significant advantage over urine and blood assay. However, it has not gained wide acceptance for a number of reasons. First, very sensitive detectors such as those based on gas chromatography are expensive. Second, the necessary odor or gaseous signatures from the volatile markers for each disease condition have not been identified. Finally, other complicating factors that need to be corrected, such as the impact from the environment and the variability from individual to individual, have not been vigorously pursued and solved. The invention described herein solves all these problems.

Applying this approach to "diagnosis" problems with equipment, the "health" of an electrical transformer can be similarly evaluated. For example, detection of PCB odor or vapor would signify that the transformer is not healthy since it is leaking a harmful substance. One can of course analyze the fluid itself for the presence of PCB, just like one can analyze markers in the blood and urine of a human body. However, the sniffing of the vapor or odor offers the advantage of "global" evaluation. If a detector is sensitive enough, it can "smell" the leaking transformer miles away, a feat that is impossible by fluid evaluation, since fluid can only be detected locally or on-site. Moreover, often more than one healthy transformer can be screened at one time at one location; whereas the local method of checking for leaking fluid has to be done item-by-item, posing potential health hazard, enormous inconvenience, and cost disadvantages. Furthermore, such odor or gas detection may be even more sensitive than PCB fluid detection, and allows the potential of uncovering developing leaks before the actual leaking of the toxic fluid itself.

The leak of the transformer depends internally on the transformer itself; for example, its construction can vary from transformer to transformer. Thus any device to be used to pick up the markers should be adaptive to the entity in order to be truly effective in evaluating the present state and/or predicting the future state of the entity. Such an adaptive system has to "learn" and accumulate "understanding" of each individual entity to do an effective job. In the case of a human being, this could be especially true. For example, if one uses pentane as a marker for lipid peroxidation and as an indirect marker for diabetic conditions within the body, one has to be aware of the possibility that pentane production and its metabolism might be different from one human being to another, even though both persons may have the same diabetic condition. In order not to misinterpret the marker, the system may have to be adaptive to each individual.

The environment surrounding an entity can have a strong impact on any diagnostic system because an entity usually does not exist by itself. It exists in an environment and thus could be linked or coupled with the environment. Thus the evaluation of the state and its progression are possibly determined not only internally by the entity but also by its existing environment. As an example, if normally the PCB odor exists even when there is no transformer leak because the transformer is located near a PCB contaminated site, then the detection or evaluation of the health of the transformer has to take into account the environmental PCB. Correction in this case may be simple, but corrections with complicated algorithms may be needed in the case of the human body because of the body's complexity. For example, pentane from the environment can be taken into the lung and come back out directly, or it can be absorbed into the tissues of the body and then desorb slowly. These pentane contributions from the lung and the tissue should not be misinterpreted as true internal production due to the intended assessment of the lipid peroxidation.

SUMMARY OF THE INVENTION

According to the invention, the state (or the health of the state) and the progression of the state of living and non-living entities can be non-invasively assessed using the values of appropriate volatile markers, provided that such markers can be identified and that the volatile substance detector can be made sensitive enough to achieve such an analysis. The detector can be based on a variety of principles which can provide very sensitive detection. Some examples are artificial olfactory systems, gas chromatographic equipment, and optical spectrometers. Also note that the "volatility" of a marker is really coupled with the sensitivity of the detector, because even a solid marker can have a vapor presses through the value may be extremely small. Thus even solid substances can be detected provided the detector is sensitive enough.

According to the invention, successful monitoring of the state might also depend on an adaptive algorithm or a computational system that can "intelligently" adapt the markers for each individual entity. One way of implementing such an algorithm is with a neural network or similar adaptive computational systems.

According to the invention, in the case that the intended marker also exists in the environment surrounding the entity and its presence in the environment is not eligible in comparison with the intended measured amount, a corrective algorithm may be needed so that the marker can be correctly interpreted.

Thus, the invention is a method of determining a set of volatile markers which are characteristic of a particular condition or disease, and which will be found in the exhaled breath of a person or odor from other parts of a body or from an entity; detecting these markers in the breath odor or gaseous emanations from the body or entity using a volatile substance detector of sufficient sensitivity; and processing the detected marker data with an algorithm adapted to the individual body or entity and also optionally (if necessary) with an algorithm to eliminate environmental and other erroneous contributions to the markers. The marker need only be as volatile as the sensitivity of the detector requires. Thus an ultrasensitive detector can detect a marker of very low volatility or concentration. The markers are selected noninvasively, i.e., they are found in emanations from the body or entity, e.g., from within the body or entity. Any number of markers may be used, depending on how well they correlate with the condition and how accurate a result is desired, i.e. general screening or accurate diagnosis/monitoring.

Accurate detection of these volatile markers is an essential part of this diagnostic system. The designs of the detectors can be broadly divided into two categories. The first one is based on ideal individual detectors. One form of implementation is a dedicated chemical sensor for each marker. This approach places a great burden on designing each sensor to respond to only one single marker but ideally not to others. The second category is based on mimicking the biological olfactory system. All the sensors or sensing elements in this artificial olfactory system could respond to the same marker, though each to a different degree. The criterion here is that the condition of the entity is recognized through the collective responses from all these "less-than-perfect" sensors that together form a unique signature for each specific condition. The tradeoff here is that may be more sensors are needed to make the signature unique, but the construction of each sensor does not have to be perfect.

The processor of the output signals from the sensors must be both powerful and flexible. A neural network is an ideal signal processor because of its ability to handle many inputs and learning characteristics. The data processing includes an algorithm adapted to the individual body in order to provide a proper baseline for the measurements. This algorithm is developed through calibration measurements which correlate detected markers to actual condition. The processing will mostly likely also include a correction algorithm to remove the effects on the markers caused by factors other than the condition being monitored. Again, a neural network signal processor is ideal for implementing the processing algorithms. The results will be a more or less accurate indicator for the condition, depending on the number of markers, degree of correlation between the markers and condition, sensitivity of the detector, and accuracy and complexity of the processing algorithms.

The methodology and apparatus can be applied to many specific situations. Diagnosis of human medical conditions or diseases, e.g. diabetes or lung cancer, is one very important application. However, the invention is not even limited to living organisms. The condition of a non-living body or system can be detected, as in the case of a leaking transformer, if it emanates detectable volatile markers or distinguishable odor or vapor signatures from a collection of markers if an artificial olfactory system is used.

DETAILED DESCRIPTION OF THE INVENTION

A. Markers

1. Supermarkers and Secondary Markers

Figure 1:
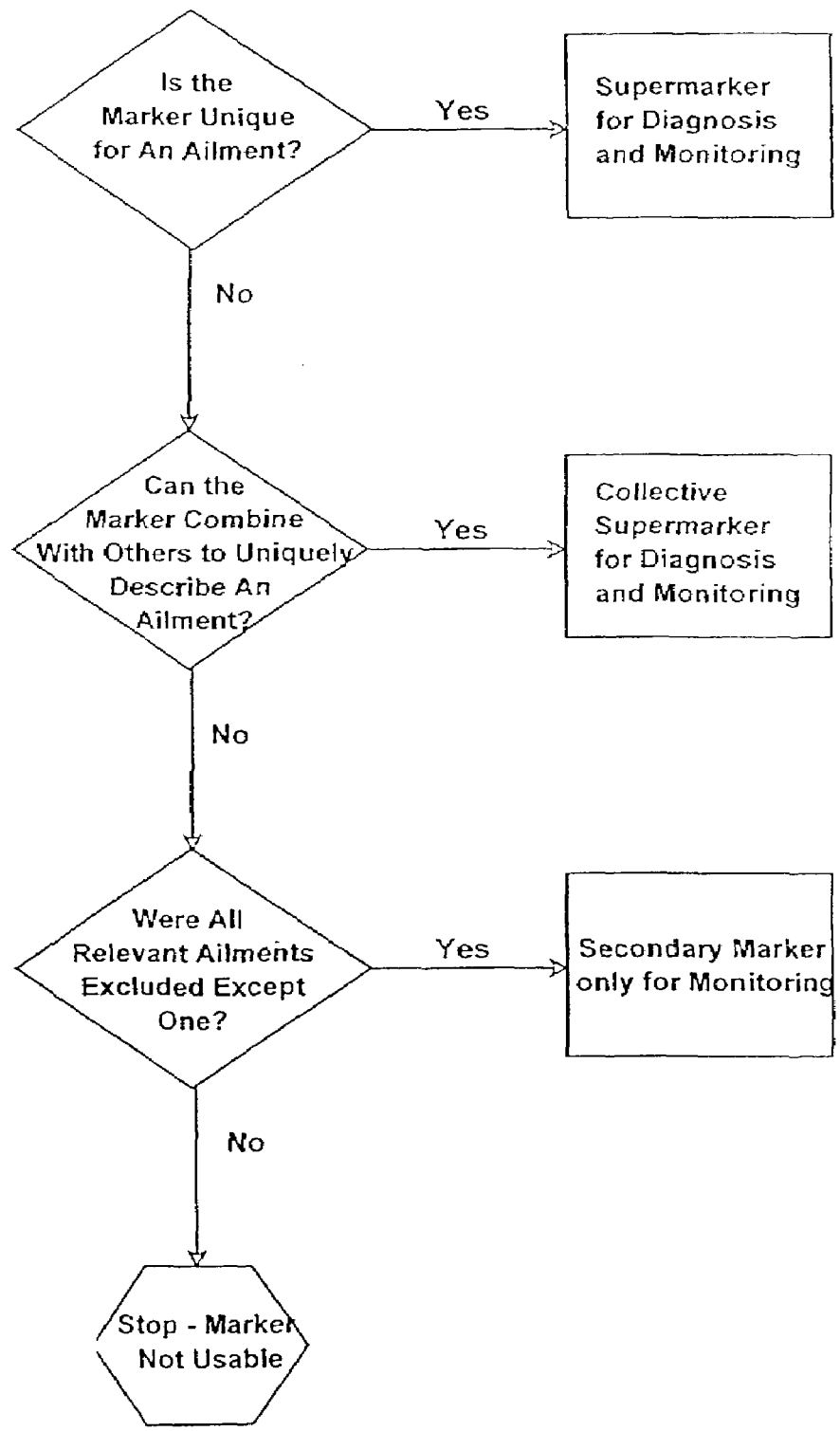
FIG. 1 is a flow chart for determining the status of a marker.

Markers are classified into two categories—supermarkers and secondary markers, either or both of which can be detected in carrying out the invention. A supermarker is one that correlates with one and only one condition. In the example of diabetes or diabetic condition, glucose is a supermarker, since a high measured glucose value is significantly correlated to a diabetic condition, and is in fact part of the definition of the disease. A secondary marker is one that corresponds to more than one condition and thus its presence would not guarantee a unique collection. In the example of diabetes, secondary markers are those such as ethane and pentane. These markers reflect lipid peroxidation, a biochemical feature of diabetes. However, increased lipid peroxidation can be due to other conditions such as liver problems. Thus elevated ethane by itself does not aid in assessment of diabetes, unless other tests have been performed to confirm this diagnosis and all other conditions have been ruled out. Only under such circumstance could be secondary maker be used to infer the target condition. Secondary markers can also be very useful in a different respect. For example, while the detection of secondary markers or the increases of their levels could not be used as a complete diagnosis for a particular disease, their presence or the enhancement of those markers coupled with other findings at a doctor's office could narrow the search for the ailment, and it also helps the doctor to justify seeking further and more expensive testing and/or referral to a specialist. For example, in the case of lung cancer, biochemical markers could provide a signature of disease that would be definitive enough for a primary care physician to ask for further tests such as computer tomography (CT) examinations. In the present days of restricted medical practice due to the confining guidelines of HMO and cost control, these signatures from appropriate biochemical markers may be enough to bridge the gap of appropriate patient care and cost containment, allowing for inexpensive screening tests that provide information diagnostic data for more thorough investigations. Since the present invention can be built at a low cost, it could function as a screening tool to predict when alternative testing should be pursued.

Thus in term of usage and applications, supermarkers can be used for both diagnostic and monitoring purposes, whereas secondary markers would only be used for monitoring, provided all conditions have been eliminated except for the target condition. In the example of diabetes, detection of glucose as a marker can be used for both diagnosing and monitoring purposes since glucose is a supermarker. Secondary markers such as pentane and ethane could only be used to infer or monitor the level of glucose when all other conditions have been eliminated. The physician has to conclude through other tests that other conditions that could cause a rise in pentane and ethane levels do not exist or are insignificant, and only under such circumstances could the elevation of these secondary markers be used for diabetic condition evaluation or glucose monitoring.

2. Collective Supermarkers

The simultaneous appearance of several markers can be very important. A set of secondary markers collectively can function exactly like a "supermarker." Such a collection is defined as a "collective supermarker." For example, if there are three secondary markers, the values of each one by itself can be affected by more than one condition; thus any one of these secondary markers cannot be used for diagnostic purposes. However, if a condition exists such that these markers will uniquely represent this condition and no other one, then collectively these three secondary markers can function just like a supermarker. This implies that they can be collectively used to provide diagnostic as well as monitoring capabilities just like a supermarker. As a result, these three secondary markers together form a "collective supermarker." Since the human body is extremely complicated, collective supermarkers could be very useful to fully characterize disease and conditions. FIG. 1 shows a flowchart on classification of markers.

3. Marker Classes

The markers can also be broadly divided into three classes. Class I represents markers that are relatively abundant and thus would be relatively easy to detect; however, if they are relatively common, these markers could be found in noticeable levels in the environment, and thus complex corrections could be needed to eliminate the background impact. Class III markers are exactly opposite. They are highly uncommon and thus either not present in the ambient or only as a negligible trace amount. No ambient correction is needed for this class of markers. However, their concentrations could be so low in the exhaled breath that they would require a much more sensitive detector. Properties of a class I marker are somewhere between those of Classes I and III. In the example of diabetics, a class II marker is pentane; whereas glucose is most likely a class III marker.

4. Metabolic Markers for Diabetes

The specific biochemistry of the metabolic markers involved in a particular disease will be critically important in the evaluation and diagnosis of a disease condition. In the following, diabetes is utilized to illustrate the invention.

Theoretically, glucose can be directly detected by a non-invasive detector with sufficient vapor or odor sensitivity because every substance, even solid, has a vapor pressure. However, again the biological system is far too complex to be characterized by one single marker; thus even if glucose can be directly monitored, it would still be desirable to monitor other markers to provide additional metabolic information that could be valuable to both the patients and the doctors. Since all these markers are coupled, some may change in values, even "preceding" the glucose level change; thus by monitoring those markers one can prevent a surge in glucose ahead of time rather than react to the hyperglycemia situation when it occurs. This will allow even tighter control of glucose level that would not be possible with just glucose measurements alone. Tight control of glucose levels will reward the patients with many more years of quality life without the numerous disabling diabetic complications as we shall discuss later. Another reason to include other markers is to ensure patient compliance with dietary recommendations.

a. Markers derived from the consideration of energy consumption

Human bodies derive energy from different sources—e.g., glucose (carbohydrates), lipid (fat), and protein. As a result of beta oxidation of fatty acids, molecules of an intermediate known as acetyl coenzyme A (acetyl CoA) is produced. Acetyl CoA does not normally accumulate in the cell, but becomes enzymatically condensed with oxaloacetate, a substance derived largely from carbohydrate (e.g., glucose) metabolism. Smooth operation of the metabolic machinery depends on the availability of sufficient oxaloacetate to serve as acceptor for acetyl CoA.

But when conditions are abnormal, the function of the metabolic machinery is impaired. In acute starvation or in impaired carbohydrate metabolism, each condition mimics uncontrolled diabetic millitus, and the supply of acetyl CoA is greater than the supply of oxaloacetate. As a result, this excessive acetyl CoA has to be handled by an alternative pathway. The cause of this imbalance is two-fold. In diabetes, faulty insulin production and/or inability to make use of insulin prevent glucose uptake into cells to provide energy for the body. This leads to excessive degradation of fatty acids by beta-oxidation in liver cells to provide energy, resulting from excessive mobilization of fatty acids from adipose cells, which in turn increases the supply of acetyl CoA. Adding to the problem, the long chain fatty acid CoA derivative inhibits the enzyme that produces oxaloacetic acid or oxaloacetate from glucose or glycogen. Therefore, in conditions that promote excessive release of fatty acids from adipose cells, ketogenesis becomes augmented.

Ketogenesis represents another pathway to dispose of acetyl CoA. Effectively, it occurs by the coupling of three acetyl CoA molecules to form acetoacetate and acetyl CoA. Some of the acetoacetate formed in liver cells usually is reduced to beta-hydroxybutyrate, but since acetoacetate is quite unstable, some decomposes to form carbon dioxide and acetone. This leads to an increase in the amounts of acetoacetic acid ($C_4H_6O_3$), beta-hydroxybutyric acid ($C_4H_8O_3$), and acetone ($C_3H_6O$), resulting in a condition known as ketosis. These three metabolites are known collectively as ketone bodies, and since the first two are acidic substances, they may cause a metabolic acidosis as they accumulate. Thus ketosis can be attributed to excessive production of ketone bodies as the body liberates large amounts of free fatty acids to override the glucose deficit.

As a result of this abnormal metabolic activity, one expects that diabetic patients will have a decrease in oxaloacetic acid, and increases in acetyl CoA, acetoacetic acid, beta-hydroxybutyric acid, acetone, and carbon dioxide. Thus these six compounds can be used as markers for diabetes. Depending on the severity of the lack of uptake of glucose, the magnitudes of the changes of these markers will correspondingly adjust. Devices that can measure these changes such as through breath analysis and can adapt to each individual patient's own metabolic rates can thus be useful to monitor the glucose status of the patients. Through these markers, neural networks can adaptively learn the relationship between these six compounds and the blood glucose concentration for each individual, and thus allow indirect measurement of the glucose level without the traditional use of invasive techniques such as using a lancet to draw blood. Again, note that theoretically direct monitoring of glucose could be possible if the detector is ultra-sensitive because any substance, even solids, would have a vapor pressure.

To fully appreciate the potential value of this invention, it is important to point out that these compounds actually provide more detailed information on the diabetic condition than just a single parameter using glucose measurement, and thus these compounds could provide very useful medical information that is typically not available using the blood glucose measurement at home. As a result, the invention is not just a replacement of the current glucose measurement device, but it goes one step further to provide patients and their doctors with many useful parameters. One such marker is acetone. Many people, even some doctors, believe that the presence of acetone in the breath, as manifested by its fruity smell, is an indicator of ketoacidosis and that normal people do not have acetone in their breaths. In reality, acetone is always present and it is one of the most abundant gases in the exhaled breath even for a normal person without diabetes. In such cases, the presence of acetone is of such a quantity that it is generally not detectable by a human nose. However, when a diabetic patient reaches the ketoacidosis state, the concentration of acetone would have risen so dramatically that a doctor will detect the characteristic fruity smell. Actually the information on acetone level together with the glucose level will point to better patient management as we will explain below. In the past it had been a medical practice to simply treat hyperglycemic patients with "more insulin." The results were usually unsatisfactory if overeating was the primary etiology of the hyperglycemia. More insulin led to more overeating and to more obesity in a positive feedback loop. More obesity led to more insulin resistance and, in most cases, the net result was that the hyperglycemia was not improved. This is generally referred to as the "diabetic clinic cycle." Thus, if glucose is greatly elevated and the acetone level is normal (10–50 nM), then the correct diagnosis of the cause of hyperglycemia is overeating rather than insufficient insulin. For optimal patient management, the most appropriate treatment would be dietary restriction and not simply more insulin. By contrast, if glucose is greatly elevated and the acetone is high (greater than 50 nM), then increased insulin would be the most advisable treatment. On the other hand, if the glucose level is under control, but acetone is high, then there is a carbohydrate deficiency condition. The proper treatment would then be to continue dieting if weight loss is the goal or reapportion the diet by adding more carbohydrate if the patient is not obese. Finally, if both glucose and breath acetone is within reason, then this is the ideal situation, and thus one should continue the present course of treatment in terms of both insulin and diet. Thus, acetone as a marker provides valuable information to both the doctor and the patient. In trying to understand the causes of diabetes, one can derive other useful metabolic markers to assess the disease and its progress and thus further improve the glucose assessment. Such an understanding can be gained through the avenue of oxidative stress, which is believed to cause the disease in its early stage, as well as its subsequent numerous complications such as atherosclerosis, angiopathy, and retinopathy. Many studies have demonstrated that oxidative stress may exert impairment via production of free radicals.

b. Markers derived from the consideration of oxidative stress

Oxidative stress may be defined as a measure of the steady-state level of reactive oxygen species (ROS) or oxygen free radicals (OFRs) in a biological system. It represents an overall equilibrium between production and scavenging of reactive species such as free radicals. A simple definition of a free radical is any atom or molecule that has one or more unpaired electrons. A free radical will attempt to gain electrons from other free radicals or molecules (i.e., reducing reagents) so as to "pair up" its unpaired electrons, and thus free radicals are chemically highly reactive. Free radicals are dangerous only if liberated in or propagated to the wrong places or in too high a concentration. Most free radical damage to cells involves oxygen free radicals, often implicated in inflammation processes and autoimmune reactions. Furthermore, oxidative stress may be amplified by a continuing cycle of metabolic stress, tissue damage, and cell death, leading to increased free radical production and compromised free radical inhibitory and scavenger systems, which then further exacerbate the oxidative stress. Abnormal increase in free radicals has been implicated in a number of diseases and medical conditions such as cancer, emphysema, asthma, hypertension, allergy, retinopathy, arthritis, aging, atherosclerosis, cirrhosis, cataract, macular degeneration, inflammation, and diabetes. For example, increases in plasma glucose concentration, as in the case of hyperglycemia, increase free radical production by one or more mechanisms such as an electron exchange reaction occurring between sugar moieties of glycated proteins and molecular oxygen.

Figure 2:
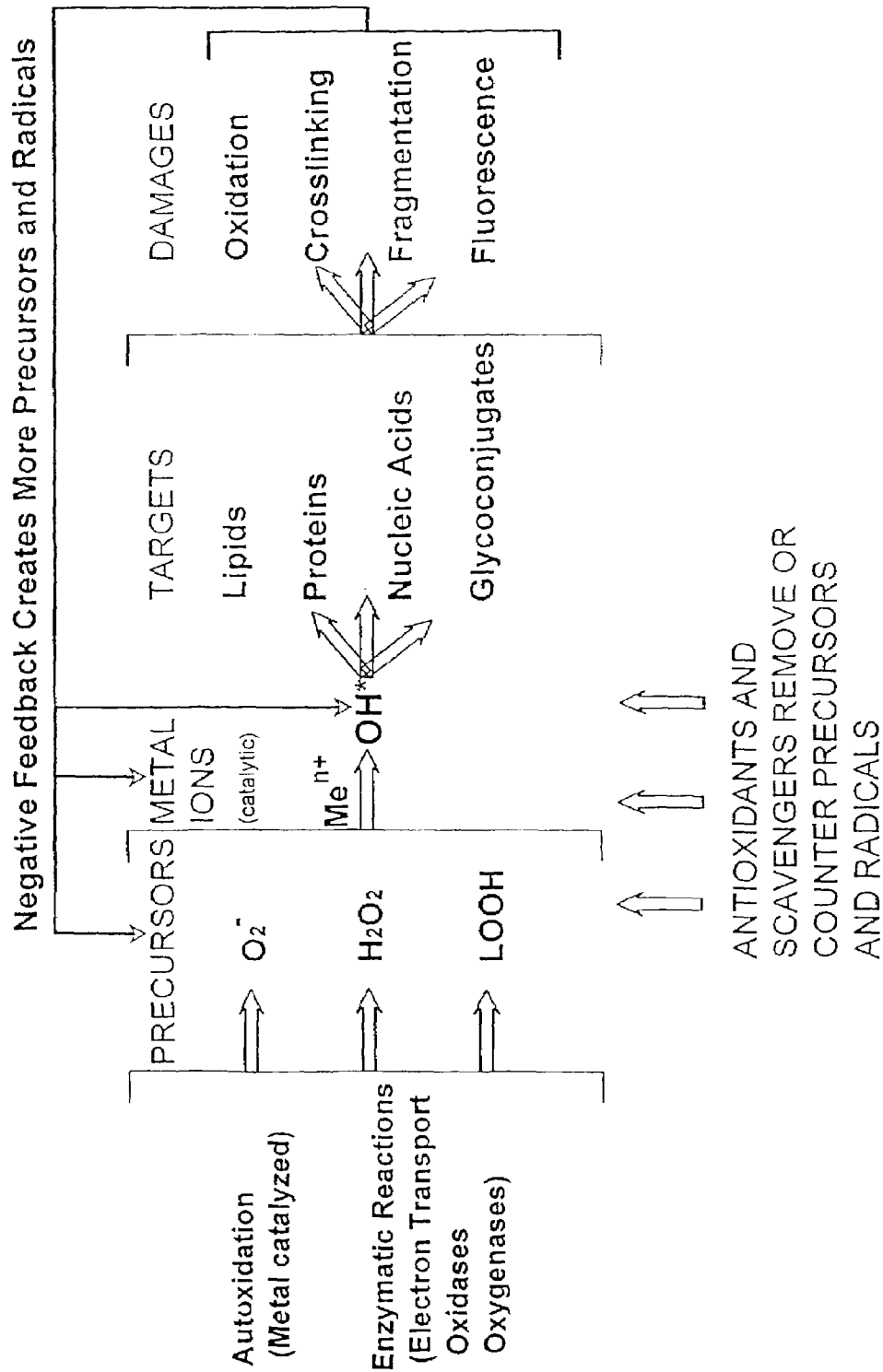
FIG. 2 shows the interaction of pro-oxidant and antioxidant species in determining oxidative stress.

FIG. 2 shows the general pathway by which increased oxidative stress may contribute to the development of complications in diabetes. Representative enzymatic and nonenzyme sources of reactive oxygen are shown. Intermediates such as superoxide ($O_2^-$), hydrogen peroxide ($H_2O_2$), and lipid hydroperoxides (LOOH) are precursors to more reactive species such as the hydroxyl radicals (OH*). Among these intermediates, hydrogen peroxide and lipid hydroperoxides could be used as markers for increased oxidative stress. Antioxidant defense systems consist of free radical inhibitors or scavengers which include enzymes such as superoxide dismutase or SOD (which destroys the superoxide radical), catalase or CAT (which destroys hydrogen peroxide), and peroxidases such as glutathione peroxidase which uses 2 molecules of glutathione, GSH, as substrate to dispose of or reduce hydrogen peroxide ($H_2O_2$+ 2GSH→GSSG+2 $H_2O$) and lipid hydroperoxides (LOOH+2 GSH→2GSSG+LOH+$H_2O$). These processes limit the accumulation of precursors. Radical scavengers limit hydroxyl radical damage by trapping reactive radicals in both hydrophilic and lipophilic (membrane) environments.

Many of these radical scavengers have already been identified and studied. Water-soluble scavengers include ascorbic acid (vitamin C), glutathione, and uric acid; lipid-soluble scavengers include tocopherol (vitamin E) and ubiquinol. However, a depletion of the antioxidant or scavenger defense system, because it has been overwhelmed by a large flux of radicals, can bring further stress to the system. Proteins such as transferrin, ceruloplasmin, and albumin also indirectly function as inhibitors by limiting concentration of free transition metal ions ($M^{n+}$), which are catalysts of many oxidation reaction that generate free radicals. As a result, damage to protein can also provoke this pathway. Thus a net flux of free radicals, representing a level of oxidative stress unchecked by a weakened antioxidant defense system, will cause chemical modifications of biological molecules. The resulting damage may affect cell and tissue functions, leading to pathology and complications. For example, lipid peroxidation due to attack of lipids by oxygen free radicals can lead to cell membrane damage.

The effect of free radicals can be highly damaging to the human body. An increased free radical production not only leads to increased damage to carbohydrates, proteins, lipids, nucleic acids, glycoconjugates, and cells, but also in turn leads to even more free radical production. This progressive worsening in the biochemical environment within the bodies of diabetics can cause increased pathology and complications as the disease progresses.

The following explains some of the more prominent mechanisms generating the excessive and damaging free radicals, leading to both the early stages of diabetes as well as the subsequent and resulting complications.

One such mechanism is an electron exchange reaction occurring between the sugar moiety of glycated proteins and molecular oxygen, operating in both the tissues and plasma of diabetic patients when their content of glycated proteins is significantly increased, resulting in the formation of glycoxidation products, $N^6$-(carboxymethyl)lysine (CML), $N^6$-(carboxymethyl)hydroxylysine (CMhL), and pentosidine, which are associated with the development of complications in diabetes. Overall, glycation of proteins may be accompanied by oxidative fragmentation of the protein, resulting in protein damage which can affect the integrity of the cell membrane, cause generation of a further supply of free radicals such as the superoxide radical, and mediate peroxidation of associated lipids which would result in lipid damage, again compromising the structure of cell membranes.

Another protein damage and free radical production mechanism is autoxidative glycosylation, which plays the role of reducing sugars such as catalysts of the oxidative chemical modification and cross-linking of proteins, leading to protein damage. The radical oxygen products formed in the autoxidation of glucose include superoxide and superoxide-free-radicals-dismutated hydrogen peroxide ($H_2O_2$) which in the presence of transition metal ions would cause oxidative damage to neighboring molecules and lead to the formation of highly reactive hydroxyl radicals. Therefore, autoxidative glycosylation is not only a reasonable mechanism for protein damage but can lead to further production of free radicals that can cause the fragmentation of proteins and also the oxidation of associated lipids during glycation reactions.

In addition to the damage to the proteins and other structures, the various free radicals and highly reactive species, such as the various peroxides, produced by the above two mechanisms (nonenzymatic glycation/oxidation (glycoxidation) and autoxidative glycosylation) would then maintain or even increase each other's activity, thus leading to mutual feedback as the disease progresses. Thus a vicious cycle of a damaging biological feedback system could occur.

Besides damaging the vital protein structures, another possibly even more significant free radical related damage for diabetes is from lipid peroxidation, an oxidative degradation of polyunsaturated fatty acids. Lipid peroxidation has been implicated in a number of biological activities including neoplastic transformation, oxygen toxicity, the formation of lipofuscin (age pigment), radiation damage, changes in enzymes and nucleotides, the modification of membrane and protein structure, and even the degradation of DNA.

Lipids are easily damaged by oxygen. Lipids containing polyunsaturated fatty acids and their esters are oxidized readily or spontaneously by molecular oxygen because of the high susceptibility of bis-allylic hydrogen to oxidation. Such an oxidation, called autoxidation, causes damage to lipids and lipid membranes of cells, and proceeds by a free radical chain mechanism.

One immediate consequence of the peroxidation of polyunsaturated fatty acids (PUFA) is their cleavage and the resulting liberation of malondialdehyde (MDA), which is a marker of oxygen free radical damage of lipids or lipid peroxidation. MDA, an aldehyde typically assayed to give a thiobarbituric acid (TBA) or thiobarbituric acid-reacting substance (TBARS) level, can make cross linkages with proteins and thus damage the protein structure. This again reveals the mutual reinforcement of protein and lipid damage. This protein damage together with lipid damage resulting directly from lipid peroxidation leads to cell degradation, especially in the cell membrane, since it is composed mostly of lipid and protein. Also, the byproducts of free radicals generated from autoxidation of lipids eventually can lead to highly reactive and biologically damaging hydroxyl radicals which can in turn further damage lipids and proteins.

The correlation between the extent of lipid peroxidation (LP) and the severity and the complications of diabetes, such as retinopathy, nephropathy, or atherosclerosis, are prominent and well-documented in the human population. As a result, one can conclude that LP in plasma, for example as measured with MDA assay in plasma, can serve as a useful monitor to judge the prognosis of the diabetic patients.

In general, studies of lipid peroxidation are consistent with studies of glycoxidation of proteins in diabetics; i.e., increased oxidation of both lipid and proteins is associated with the development of diabetic complications. More importantly, lipid peroxidative damage may not be limited to the lipid compartment, because as stated above, lipid peroxides may cause browning and cross-linking of proteins such as collagen and may contribute to the development of fluorescence in plasma proteins and possibly collagen in diabetics. Thus, increased glycation of collagen and plasma protein in diabetics may stimulate the oxidation of lipids, which in turn stimulates autoxidative reactions of sugar (glucose). This enhances damage to both lipids and proteins in circulation, thereby continuing and reinforcing the cycle of oxidative stress and damage. Thus, in fact oxidative stress may be a common pathway linking diverse mechanisms for the pathogenesis of complications of diabetes.

It is also clear that damage to protein can provoke oxidative stress not only through enhancement of lipid oxidation, but possibly also through the changing concentration of the free transition metal ions which readily catalyze reactions involving $H_2O_2$ and free radicals.

Damaging effects of OFRs at the fundamental level involve the DNA structure an thus might also explain the acceleration of aging, which is one of the most salient features of diabetes. Denaturation of proteins by OFR reactions may be a factor in the tendency to form autoantibodies. As stated above, OFRs may induce degradative effects on lipids or proteins of the nervous system, fostering the development of polyneuritis and retinopathy. Toxic effects on endothelial cells and vascular walls may contribute to microangiopathy and atherosclerosis.

Oxygen free radicals are not only involved in long-term complications for diabetics, but they are considered likely to participate in the very early stages of the disease through the autoimmune destruction of insulin producing pancreatic beta cells.

A 1998 study in young diabetic patients showed that systemic oxidative stress is present upon the early onset of type 1 diabetes and is increased by early adulthood. Decreased antioxidant defenses may increase the susceptibility of diabetic patients to oxidative injury. Lipid peroxidation was assayed through plasma MDA, which showed that TBA level increased significantly in DO subjects (diabetic onset group evaluated 7–10 days after the clinical onset of diabetes, when hydroelectrolytic disorders and acidosis had returned to normal with therapy). TBA rose even further in the DA subjects (adolescent and young adult diabetic group diagnosed 2–22 years earlier and who were free of clinical symptoms of neuropathy, nephropathy, and retinopathy) when compared with control subjects. This demonstrated for the first time the elevated concentration of plasma MDA, an end product of polyunsaturated fatty acid peroxidation, only 8 days after clinical onset of diabetes.

In the same study, the determination, of protein carbonyl group (PCG) levels in plasma revealed the same pattern. Proteins are among the main targets of oxidation when there is an increase in OFR, and increased carbonyl content in protein from aldehyde and ketone formation is an indicator of oxidative stress. Here, plasma PCG levels were significantly higher at the onset of diabetes and in diabetic adolescents without complications compared with control subjects, which would also indicate that free-radical-mediated oxidative damage of proteins is produced at diabetic onset and tends to increase in later stages of the disease. Carbonyl group formation is considered an early and stable marker for protein oxidation, and is a method used for assessing metal-catalyzed oxidation of protein.

Impairment of the antioxidant system in diabetics is shown in the same study by initial increases in SOD activities as a compensatory activation mechanism due to increases in superoxide radical generation at the onset of diabetes followed by subsequent decrease in SOD activity in diabetic adolescents which suggests that with longer disease duration, SOD induction and consequently its activity progressively decreases.

Diabetes can also be produced in animals by the drugs alloxan and streptozotocin (STZ). The mechanism of action of thee two drugs is different, but both result in the production of active oxygen species, again substantiating the involvement of free radicals and the resulting metabolic perturbation in diabetes such as an increase in MDA levels.

The overall picture thus far is that active free radicals may induce a diabetic state at the onset which leads to an increase in active oxygen species production, and thus further aggravates the biological system through weakening of the antioxidant defense system, leading finally to the pathological conclusion and complications. For monitoring purposes, MDA, a significant end-product of lipid peroxidation, reflects the diabetic condition and progress in both animal and human models, and thus can serve as a useful monitor or marker.

Besides using an MDA assay to assess lipid peroxidation, on can also detect lipid peroxidation through hydrocarbon gases. Lipid hydroperoxide generated from lipid peroxidation decomposition into alkoxy radicals (LO*).

$$LOOH + M^{+n} \rightarrow LO^* + OH^- + M^{+(n+1)}$$

This is followed by beta-scission and hydrogen abstraction resulting in the formation of hydrocarbon gases. Beta-scission of alkoxy radicals is a well-known process and involves unpairing of electrons in the bond located beta to the free radical. This process generates hydrocarbon free radicals and stable carbonyl (—CO—) compounds. For example, ethane and pentane are produced via beta-scission from the n-3 and n-6 fatty acid families, respectively, through peroxidative decomposition. Beta-scission yields an ethyl radical and pentyl radical from n-3 and n-6 fatty acids respectively which can then react further. Abstraction of hydrogen by the ethyl or pentyl radical then yields ethane and pentane respectively.

This basic understanding again leads to conclusion that glucose measurement may not be the best marker for the status of diabetic conditions. Biological systems are complex, and thus it is illogical to use only a single parameter to reflect their complexity. A number of parameters or markers can be used to more accurately describe the patient's status. These markers, including hydrogen peroxide, lipid hydroperoxide (LOOH), $N^\epsilon$-(carboxymethyl)lysine (CML), $N^\epsilon$-(carboxymethyl)hydroxylysine (CMhL), pentosidine, certain aldehydes such as MDA, and certain hydrocarbon gases such as ethane and pentane together with classic metabolic markers such as oxaloacetic acid, acetyl CoA, acetoacetic acid, beta-hydroxybutyric acid, acetone, and carbon dioxide, would provide a more complete assessment of the patient's condition. Through the use of a neural network or other intelligent system individually calibrated to the patient's glucose level, one can then also infer the glucose status as well as providing a detailed analysis of the internal state of the patient. Providing a more comprehensive suite of information would be highly beneficial to both the patient and the doctor in terms of developing an optimal regime of therapy.

The exhaled breath is a voluminous and readily accessible waste product. Though not as complex as urine or blood, breath is known to contain at least a few hundred complex molecules present at nanogram/liter quantities (Krotoszynski 1997 and 1988). Breath analysis is less intrusive than that of urine and far less upsetting than poking a lancet or a needle to draw blood for laboratory analysis. Among the complex molecules presented in expired air, the aliphatic hydrocarbons of lower molecular weight are the simplest. They are nonpolar substances that, at ambient temperature, are gases or highly volatile liquids. Because of their nonpolarity, they are only minimally water-soluble, and would thus be readily exhaled in the expired air.

The analysis of breath odors is rather complicated. It is important to observed early on that expired hydrocarbons represent various combinations of possible ambient air hydrocarbons cycled through the lung, as well as hydrocarbons released from body stores and those metabolically produced, e.g. through lipid peroxidation, all of which may be modulated by hepatic metabolism. These complications are illustrated briefly in detail using breath ethane and pentane as examples, for these two volatile markers are well documents in research literature. More than 200 publications have documented the exhalation of ethane and n-pentane both in animals and in humans. The straight-chain aliphatic hydrocarbons ethane and pentane found in human breath have been advocated as non-invasive markers of free radical-induced lipid peroxidation in humans undergoing oxidative stress, and thus they become indirect markers for diabetic status. In in-vitro studies, the evolution of ethane and pentane as end products of n-3 and n-6 polyunsaturated fatty acids, respectively, correlates very well with other markers of lipid peroxidation, and even seems to be the most sensitive test available. In laboratory animals the use of both hydrocarbons as in-vivo markers of lipid peroxidation has been validated extensively. Although there are other possible sources of hydrocarbons produced as in-vivo markers of processes such as protein oxidation and colonic bacterial metabolism, these apparently are of limited importance and do not interfere with the interpretation of the ethane and pentane breath test. Furthermore, the results of the hydrocarbon breath test are not influenced by prior food consumption. Nevertheless, the long-term use of a diet high in polyunsaturated fatty acids, such as in parenteral nutrition regimens, may result in increased hydrocarbon exhalation. This is reasonable since there is an increase in the substrate available for peroxidation.

Hydrocarbon excretion slowly increases with age. Short-term increases follow physical and intellectual stress and exposure to hyperbaric dioxygen, possibly because of the extra intake of oxygen, enhances the oxidation process. And both vitamin E and beta-carotene supplementation decrease hydrocarbon excretion. This may reflect a boost to the antioxidant defense system, which thus should decrease the availability of free radicals for damage such as lipid and protein oxidation, and thus could lead to a decrease in the production of ethane and pentane. So one should be aware that while some of these changes, such as aging effect, may have nothing directly to do with diabetic conditions, other changes such as those due to vitamin E intake could affect the diabetic condition, and thus correspondingly change the exhalation of ethane and pentane.

The production of hydrocarbons relative to that of other end products of lipid peroxidation depends on variables such as the local availability of certain metal ions which act as a catalyst, and also dioxygen. In addition, hydrocarbons are metabolized in the body, which especially influences the excretion of pentane. Because of the extremely low concentrations of ethane and pentane in human breath, the breath test requires a careful technique.

There is general agreement that the best volatile breath markers for lipid peroxidation in vitro as well as in vivo are ethane and pentane, alone or in combination. Ethane and pentane are products of lipid peroxidation. Ethane was shown to be almost exclusively derived from peroxidized n-3 polyunsaturated fatty acids, that is, linolenic acid and derivatives. Likewise, peroxidation of n-6 polyunsaturated fatty acids, like linoleic and arachidonic acids, results mainly in the formation of pentane. These two classes (n-3 and n-6 PUFAs) represent the great majority of polyunsaturated fatty acids in the body. Other PUFAs include n-4, n-7, and n-9 fatty acids but they are relatively minor components.

If ethane and pentane are accepted as markers for lipid peroxidation in vivo, what is the certainty that these two hydrocarbons do not originate from other metabolic processes in the body? Researchers have found that the available evidence is strongly in favor of peroxidation of polyunsaturated fatty acids as the major, if not the only, endogenous (originating or produced within the organism or one of its parts) source of the hydrocarbons ethane and pentane found in breath.

But the most important point here is that ethane and pentane productions were found to correlate well with the formation of lipid peroxides, conjugated dienes, malonaldehyde, urinary malonaldehyde, and thiobarbituric acid substances, all of which are products of lipid peroxidation and are used in studies of lipid peroxidation. Laboratory work has provided an impressive body of evidence that ethane and pentane evolution adequately reflects lipid peroxidation, which is associated with the diabetic condition. However, it is important to point out that abnormal excretion of these hydrocarbons could have come from other medical conditions such as certain liver disease. Thus it is vital that these conditions be ruled out, and/or that other markers be used in addition to these two hydrocarbons.

Given that ethane and pentane reflect lipid peroxidation, the use of these two markers could still be complicated by both internal and external factors. Internal factors include the impact of oxygen and iron, which can affect the production of these hydrocarbons during the course of lipid peroxidation, as well as their metabolism, which converts the generated hydrocarbons into carbon dioxide. Finally, clearance from blood and lungs could also affect the exhalation of these hydrocarbons. External complicating factors include exercise, diet, drugs, and the impact of existing hydrocarbons in the ambient air.

It is important to point out that the peroxidative pathway for in-vitro study shows possibilities other than the excretion of ethane and pentane. Higher dioxygen levels can promote the formation of ethanol and 1-pentanol instead of ethane and pentane from beta-scission. As a result, it may also be important to monitor the presence of ethanol and 1-pentanol in addition to ethane and pentane because of the potential influence of dioxygen. Transitional metals, a catalytic factor for a number of relevant reactions, though varying from individual to individual, are believed to be in dynamic or quasi equilibrium for each individual. Thus, if a system is calibrated and adaptive to each individual, then this factor should not affect the successful outcome of the monitoring.

To develop a useful analytical model, two issues must be taken into consideration regarding metabolism. First, it is reasonable to assume that the production and the metabolism of the hydrocarbon should be at equilibrium when there is no external perturbation. Since diabetic glucose measurements are typically done before metals (an external perturbation), an equilibrium should be reached when the device attempts to measure the outcome. This equilibrium represents a characteristic signature of the glucose level for an individual. The second issue is the variability of both hydrocarbon production and metabolism from individual to individual. When an intelligent adaptive algorithm that learns the physiological conditions of each individual, one does not have to take into account such variability from patient to patient, since the device is individually adapted. It is only necessary to recognize the pattern signature for each glucose level that corresponds to each individual. Since the sensor collects information for ten or more parameters, it is highly unlikely that two or more different signatures from these parameters could correspond to a single glucose level. Even so, such a situation can be overcome with an adaptive algorithm, since it can certainly map two or more sets of inputs to one single outcome. Inversely, it is virtually impossible that one single signature from an individual can correspond to different glucose levels, because the measured parameters are biochemically linked to the glucose levels.

The breath concentrations of exhaled hydrocarbons like ethane and pentane might be dependent on the efficacy of their clearance from the blood within the lungs. The effects of lung blood flow and lung function on hydrocarbon excretion in the rat and human have been studied, and the hydrocarbon excretion was not influenced by variations in minute ventilation with the exception of lung abnormalities.

The following reviews the external factors that might influence the production of ethane and pentane. These include diet, exercise, and smoking.

In the only study found on hydrocarbon production of humans as a function of diet change, the result is reassuring. A single standard breakfast containing 12.9 g and 0.4 g of linoleic and linolenic acid, respectively, did not change ethane and pentane concentration in the exhaled air composed to the fasting state. Similar studies on rats also support such findings. While extreme diet conditions, such as a high dextrose diet, leading to acute hyperglycemia, would lead to an upsurge in the exhalation of ethane, this upsurge may exactly reflect the deterioration of the diabetic condition, which is thus correctly shown by an increase in ethane production and detection. Since a normal diet is not so extreme, especially for diabetic patients who have to follow rigid diet guidelines, one can be assured that ethane production fluctuations due to a variation in diet will be minimal and statistically insignificant, and thus would not prevent using ethane as a marker. In addition, one expects the body to act as a buffer, and thus would not anticipate any significant fluctuation in ethane production in normal circumstances. Moreover, since glucose measurement is typically done before meal times, the body will essentially behave the same at the same time of the day, resulting in consistent behavior unless the glucose level fluctuates. In fact, if a patient goes on a food binge and intakes inappropriate macro-nutrients in extremely large quantity, the sensors will deviate, and thus put out an alert for such detrimental behavior.

In some cases, measurement right after exercise is not advisable because physiologic stress may mobilize tissue stores of these alkanes, resulting in an increase pulmonary excretion of n-pentane that may not represent lipid peroxidation, but merely the passive washout of previously equilibrated exogenous, environmental n-pentane from muscle caused by increased blood flow. While exercise would change the output of pentane, ethane showed no increase following exhaustive exercise, suggesting that ethane detection may not need any environmental correction. This makes ethane possibly a better marker.

Variability with time is also little more than a minor complication. Day-to-day variability as measured on a normal human subject has been reported to be ±10%, suggesting that ethane essentially remains constant or stable as a function of time, and is not much perturbed by factors such as the levels of dioxygen and transition metals. This result supports the premise that hydrocarbons in exhaled breath remain relatively constant in normal individuals.

Smoking is an important source of several hydrocarbons, among which are ethylene, propene, propane, ethane, and pentane. Smoking thus can significantly alter the result. However studies on hydrocarbon production among smokers reveal that 3 hours after puffing a cigarette, hydrocarbons essentially drop back to an equilibrium, suggesting that with appropriate precautions, the technique should work even for smokers.

After all these considerations, it is important to point out that the expired hydrocarbons are extremely small in quantity and thus the devices used should be very sensitive. The yield of pentane is very low. In-vitro production is ~0.1% of malonaldehyde production. In the rat, in-vivo yield is about 0.2 mmol per mol of lipid peroxides. Since some of the major sources of polyunsaturated fatty acids in the body are linoleic acid and arachidonic acid, which are both of the n-6 family, pentane results in a 2.5 times higher response than that of ethane when a flame ionization detector is used for an in-vitro study. This is significantly because hydrocarbon assessment may be performed without previous washout or background correction. Thus depending on the local circumstances, ambient pentane concentrations may be low enough to do such measurements reliably. But the body does contain n-3 polyunsaturated fatty acid, which is the source for the formation of ethane.

As a metabolic marker, ethane has one great advantage over pentane because ethane, unlike pentane, is not metabolized by the liver, and thus one has to deal with one less complicating factor. As a result, it seems logical to use both markers to reflect the major lipid classes. It can also be hypothesized that the sensitivity and specificity of the test may be improved by combining both markers because of an enhanced capacity to discriminate between non-specific and lipid peroxidation-induced increases of hydrocarbon excretion. In real life, when both hydrocarbons are assessed, the values found for ethane are comparable to those found for pentane.

Unfortunately the air that we breathe is very seldom hydrocarbon free. Thus, hydrocarbons in ambient air might have to be take into account. There are two body storage reservoirs for hydrocarbons from the ambient air—the lung and the viscera/muscles/tissues/fat. Actually the contribution from ambient air and from these storages is not important as long as these factors do not vary, since the artificial neural network (ANN) will take care of these contributions for each individual. But the ambient hydrocarbons could vary. For practical consideration as a clinical tool, researchers either neglect the problem of ambient air contamination completely or deal with it by a simple correction for actual background concentration. However, such a simple correction is only sufficient to remove most of the effect of ambient air on the lung but not necessarily all. It does not take into account the past history of the ambient air, which affects the body storage in the muscle, fat and tissue. In certain cases, simple corrections without taking into account the past history may already be sufficient. In this invention, the accumulated effect of the ambient air on the internal storage will be corrected as follows if deemed necessary, thus providing even greater measurement accuracy.

As stated above, there are two different gas-reservoir types in the human body. The first one is the lung, which has a relatively fast response. The second reservoir is the body storage provided by the muscles, tissues, and fat, which has a relatively slow response. Another part of this invention is an approach to solve these environmental complications. First, each patient has to establish a washout curve for each of the markers at the doctor's office. Essentially breathing clean air provided at the doctor's office, one can eliminate the environmental contributions of the markers through monitoring the decay of the value of each of the desired markers from the exhaled breath. Initially, the value of each of the markers will drop very fast reflecting the purging of the lung. This will be formerly by a slower decay reflecting the output from the tissue storage. Finally, the value will reach a plateau that represents the true internal production of that marker. Such a time dependent behavior is represented by the equation, $aw(t)+b$, where a is the scaling factor that depends on the ambient concentration and b is the true internal production. By measuring the ambient concentration of each of the markers, one can then deduce the washout curve or function, $w(t)$, for each of the markers. These functions will be used during routine monitoring to correct for the unwanted contributions from the lung and the tissues.

Each of these washout curves essentially will remain constant in shape provided the body does not change substantially; for example, the weight of the patient may have to remain relatively constant. Each of these curves may, however, scale differently as indicated by a scaling factor due to different environmental conditions and shift upward and downward due to different internal production.

The actual implementation of this approach is quite simple. During deployment, the patient would breath clean air briefly to simulate the washout condition during which a few measurements for each of the markers would be made. These few (a minimum of two) points for each marker would then be used to fit the curve or the function, aw(t)+b, constrained by the shape of the established washout curve, w(t), for that marker. Though a minimum of two points is needed, to reduce the impact of noise a minimum of three points is preferred. From such a fit, the internal production can then be calculated for each of the markers. Since the initial measurements are made in a region of rapid changes (initial fast drop), the measured values will be far apart, and this will help to accurately establish the internal production value. Also, the measurements can be made in succession and thus shorten the total time of measurements, since the values change so rapidly. An internal algorithm can continuously fit the curves based on each newly-acquired data point for each marker. Once all the fits are accurate enough, the device can automatically signal the patient to stop breathing into the device.

A simpler method may be used once the washout curve is established in the doctor's office. Assuming equilibrium between patient and environment, measurement of the ambient markers determines an environmental correction. If nonequilibrium, the ambient markers are sampled over a period of time to establish effective average environmental corrections.

Thus, the non-invasive nature of hydrocarbon assessment renders the hydrocarbon breath test a promising technique of assessing lipid peroxidation and oxidative stress in humans. It may be very helpful in quantifying peroxidative damage as well as assessing the response to therapeutic and preventive strategies in a given clinical condition such as the case of diabetes.

The work of other researchers supports the feasibility of the hydrocarbon breath test. The validity is using ethane and pentane as markers for diabetes can be shown by using data from the work of M. P. Habib and O. M. Pitaknen, M. P. Habib reported in 1994 a study of ethane exhalation and plasmid glucose level in control and diabetic rats divided into five groups (control, saline-injected normal rats, insulin-treated diabetic rats, diabetic rats, and glucose-injected normal rats).

Figure 3:
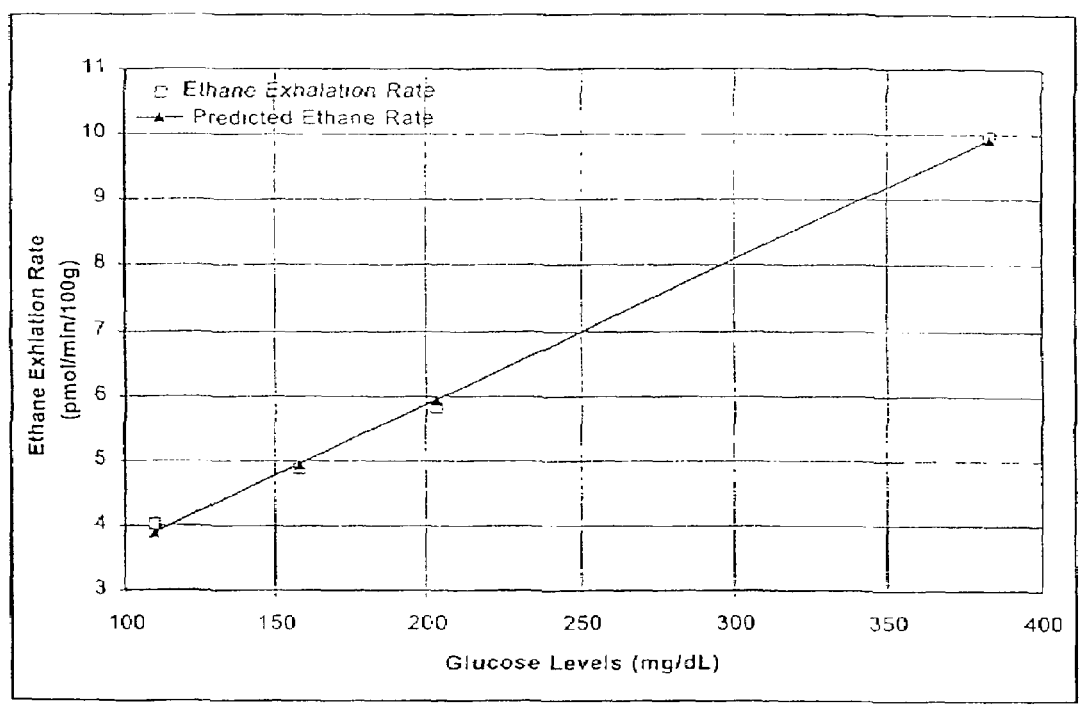
FIG. 3 shows a linear relationship between exhaled ethane and glucose levels in rats.

A linear relationship between glucose levels and ethane production rate is revealed after further analysis by Applicant and is shown in FIG. 3. The curve fitting was done wit the data point from the group with saline injection missing. The reason for such a deletion is that there is no medical basis for saline injection to afford the diabetic condition, and thus the corresponding increase in glucose is due to reasons other than the diabetic condition. Even if such a point is included, the linear fit is only negligibly affected.

It is clear from FIG. 3 that chronic uncontrolled hyperglycemia as in the case of diabetes or acute hyperglycemic excursions is associated with an increase in in-vivo lipid peroxidation as measured by exhaled ethane. It is also clear from the graphing of these data that the ethane production rate is precisely correlated with the plasma glucose level. This provides direct evidence that ethane exhalation rate not only is an effective marker for diabetic condition and hyperglycemic excursions through lipid peroxidation, but even more importantly, that it can be used to monitor plasma glucose levels without invasive procedures. The linear regression provides an excellent data fit. It also implies a 10% error in ethane measurement will result in only an insignificant 4.5 mg/dL error in glucose measurement, suggesting that one can accurately predict glucose levels with acceptable tolerance. (Typical test strips used in current diabetic monitoring system are at best accurate up to 20 mg/dL which is four to five times higher than the 4.5 mg/dL.) This result provides a solid confirmation for the present approach.

While the data representing these 5 groups as shown in FIG. 3 is validating, however within each independence group no significant correlation between glucose level and ethane exhalation rate was found. This is probably due to the small variation in the glucose levels within each particular group. The situation is compounded by a small sample size (just 12 rats for the diabetic group). Even more important, the individual fluctuations or variability from individual to individual makes it impossible to study the relationship between glucose levels and ethane exhalation within each group. This individual variability was confirmed by S. Morita. He studied pentane in the breath of 15 healthy humans in 1986, and found that n-pentane excretion varied ten-fold among healthy individuals. Thus this might explain why no one has attempted to use breath analysis for glucose monitoring, because without an adaptive neural network or equivalent algorithm to learn and adapt to the behavior of each individual, the individual variability would render such a task impossible. Another equally important reason is that the use of high performance liquid chromatography (HPLC) or gas chromatography (GC) for breath analysis is definitely not cost-effective. This is especially true to deliver an affordable home testing device. However, in the present case, modified neural network algorithms are used to learn the glucose-volatile marker relationship for each individual. This variability from individual to individual would be accounted for by the adaptive algorithm, and an artificial olfactory system is expected to be a very cost-effective sensing system. This combination would make low-cost, totally non-invasive glucose measurement both technically possible and economically feasible.

The close association of expired pentane with the diabetic state has also been confirmed. Similarly, O. M. Pitkanen's 1992 study of expired pentane in diabetic rats found that the expired pentane for some diabetic rats increased even before the manifestation of the disease, and in all cases, pentane continued to rise as time and disease progressed. This is important because one may use the level of pentane or other similar markers to predict a rise in plasma glucose even before such an increase occurs. Tight control of glucose level through frequent measurements and corrections of its levels has been shown to result in a substantially delay in diabetic complications and thus add many years of quality life to a patient as well as reducing the cost of patient care. If one can "predict" an increase in the glucose level ahead of time, as may be possible through monitoring of relevant markers, this should result in even better control and thus lead to better patient care. However, in the same study for those normal rats that were made diabetic using streptozotocin (STZ), a chemical that causes diabetes, expired pentane remained low, suggesting there is a fundamental difference between the two cases.

These findings could possibly be explained as follows. Diabetes and its complications are partly attributable to the destruction or the impairment of islet cells and cell membranes such as erythrocyte membranes. There are possibly two avenues for such destruction and impairment. Chemicals, such as STZ, could possibly directly destroy the islet cells within the pancreas. For this particular case there may be no damage to the cell membrane due to lipid peroxidation or protein oxidation, and thus those corresponding markers, such as pentane, would not show an increase. However, for the case of diabetes not caused by chemicals, the destruction and impairment of islet cells may be achieved first through degradation of the cell membrane by free radicals. Once the cell membrane is sufficiently degraded, islet cells will be affected and thus lead to diabetes. The cell membranes being affected are not just restricted to those of the islet cells but also other cell membranes such as those of the erythrocytes. Researchers have shown abnormal lipid content due to high level of polyunsaturated fatty acids of erythrocyte membranes in diabetic patients for both Type 1 and Type 2 diabetic patients. Thus, diabetic erythrocyte membranes are more readily oxidizable than those of control subjects. In the process of membrane degradation, inflammation occurs and is revealed in histology examinations as have been reported in the literature. The process of membrane degradation is due to lipid peroxidation and/or protein oxidation which result in the production of MDA, ethane, pentane, and related markers. Thus for non STZ-induced diabetes, expired pentane may be observed even before the onset of diabetes, as demonstrated by Pitkanen in the diabetic rat model. However, the degradation of the cell membrane through lipid peroxidation may not be the direct cause of diabetes. It is possible that in addition to or in place of direct damage due to free radicals, some of the products of lipid peroxidation such as the highly toxic MDA and other aldehydes (for example, HNE) are also responsible as explained herein. Thus decrease in certain lipid peroxidation, resulting in less production of certain toxic aldehyde substances, could protect or delay diabetic conditions. This is exactly what has been found in rats deficient in n-6 fatty acid. The deficiency protects the rats from diabetes.

Finally and very significantly, Wang and his coworker in 1997 have successfully used an electronic nose to distinguish diabetics from normal people. They described using a sensor array consisting of only five sensors to test the expired gases and odors from 32 volunteers—18 diabetics and 14 normal persons. Their sensing technology is based on modified traditional $SnO_2$ sensors. Testing was performed before a meal, 0.5 hour after a meal, and 1 hour and 2 hours after a meal. Simultaneously blood sugar was measured as a comparison. Using a fuzzy clustering algorithm, they clustered the results into two classes, with class I having a high correlation with diabetics and class II corresponding with normal people. Their results are summarized in Table 1 below.

TABLE 1

| | Test time | Number with higher blood sugar | Number classified by exhaled breath in class I |
|---|---|---|---|
| Diabetes | Before meal | 12 | 11 |
| | 0.5 hour after meal | 14 | 13 |
| | 1 hour after meal | 18 | 18 |
| | 2 hours after meal | 16 | 16 |

As can be seen, their electronic nose correctly identified those diabetics having higher blood sugar in all the cases (100%) one and two hours after meal. The identification is excellent but not perfect for the other cases before meal and 0.5 hour after meal with diabetic patients. This is certainly understandable since the differences in blood glucose for diabetes and normal subjects are typically substantial one and two hours after meal, but differences are much smaller before meal and 0.5 hour after meal, as can be seen in the summary in Table 2 which shows the direct blood glucose measurements.

TABLE 2

| Test time | Diabetes (glucose conc.) | Normal (glucose conc.) | Difference |
|---|---|---|---|
| Before meal | 100 | 81 | 19 |
| 0.5 hour after meal | 128 | 112 | 16 |
| 1 hour after meal | 191 | 70 | 121 |
| 2 hours after meal | 210 | 78 | 132 |

A wide variety of volatile substances are present in exhaled breath, other than ethane and pentane, so other markers are also likely to be involved as further described herein. For example, n-pentane is always a minor component and amounts to a mean value of 5% of isoprene. Polyisopropenes, e.g., the ubiquitous squalene, are possible sources of isoprene via a radically-mediated, in-vivo peroxidation. All mechanisms which induce, directly or indirectly, an increased rate of reactive oxygen intermediates and are also thought to attack the integrity of membranes via mechanisms of lipid peroxidation might also attack polyisoprenes, with the consequence that both isoprene and n-pentane are produced. Thus in parallel with pentane, another possible volatile marker is isoprene.

In addition to previously described hydrocarbon markers, markers also are available in the aldehyde chemical family. The most notable one is MDA, which has already been confirmed to be an effective marker for lipid peroxidation, though MDA is not a volatile chemical. However, MDA is not the only aldehyde resulting from lipid peroxidation. Some of the other aldehydes produced are volatile and some are biologically active and can produce a number of deleterious effects in cells because they exhibit cytotoxic, hepatotoxic, immunogenic, mutagenic, and genotoxic properties. Other than MDA, biologically active aldehydes include 4-hydroxynonenal (HNE) from n-6 PUFAs and 4-hydroxyhexenal (HHE) from n-3 PUFAs. Several of these reaction products such as 4-hydroxynonenal are themselves able to propagate the lipid peroxidation process. In addition, other hydroxyalkenals, as well as alkanals, 2-alkenals, 2,4-alkadienals, and some other aldehydes represent the cytotoxic aldehydes generated by peroxidizing microsomes. It is reasonable to assume that aldehydes produced in-situ in living tissues are partially involved in the physiopathological consequences of lipid peroxidation. Thus in addition to the primary free radicals which initiate lipid peroxidation, some of these aldehydes can be viewed as secondary toxic messengers. The main mechanism for the formation of aldehydes from lipid hydroperoxides is homolytic scission (beta-cleavage) of the two C—C bonds on either side of the hydroxyperoxy group.

The principle poly-unsaturated fatty acids (PUFAs) in mammalian tissues and cells are n-6 linoleic acid (18:2), n-6 arachidonic acid (20:4), and n-3 docosahexaenoic acid (22:6). The volatile aldehydes that have been reported during the course of autoxidation of arachidonic acid include hexanal, 2-octenal, 2-nonenal, 2-heptenal, 2-hexenal, 2,4-decadienal, pentanal, 2,4-nonadienal, and the key non-volatile aldehyde 4-hydroxynonenal. Among them, hexanal appears to be the major volatile aldheyde from the n-6 PUFAs. Its values reflect a variation in this n-6 PUFA content of low-density lipoprotein (LDL) which consists of a mixture of PUFAs, as well as variation in the rates at which they compose. By contrast, propanal is the major aldehyde formed from n-3 PUFAs. Linoleic acid constitutes 92% of the polyunsaturated fatty acids in LDL, and identified volatile aldehydes through the peroxidation process include not only hexanal, propanal, and pentanal, but also butanal. Thus, within the aldehyde families, the four most volatile markers used in this invention are hexanal, propanal, pentanal, and butanal.

Finally, protein oxidation would also play a role in diabetic development, and 2-methylpropene (isobutene) formation was suggested to be the result of free-radical induced oxidation of proteins rather than lipids. Thus isobutene would be another marker for this invention for diabetic monitoring.

Measurements of the susceptibility of LDL to oxidative stress have been based on determinations of thiobarbituric acid-reacting substances (TBARS), conjugated dienes, fluorescent products, and peroxide values. These methods are, however, complex assays that lack specificity and measure a great variety of compounds. Chemically more specific measurements also have been used to measure oxidative modification to LDL, including specific aldehydes by high performance liquid chromatography (HPLC) as previously indicated. However, this method has two problems—it is an indirect method relying on the formation of hydrazone; and HPLC is an expensive and complicated technique that can only be performed by professionals in laboratory settings. This renders such a method unsuitable for eventual home detection and analysis. Other methods such as GC are also too tedious and expensive for routine analyses of oxidative susceptibility. As a result, detectors based on biological olfactory systems can be a very effective tool for non-invasive glucose monitoring, as well as monitoring other relevant clinical indicators of a diabetic patient through such volatile markers as carbon dioxide ($CO_2$), acetone ($CH_3COCH_3$), hydrogen peroxide ($H_2O_2$), ethane ($C_2H_6$), ethanol, pentane ($C_5H_{12}$ or methylbutane), pentanol, isoprene ($C_5H_8$, 2-methylbuta-1,3-diene), hexanal ($C_6H_{12}O$ or caproaldehyde or n-caproic aldehyde), propanal ($C_3H_6O$ or propional or propionaldehyde), pentanal ($C_5H_{10}O$ or valeral or valeraldehyde), butanal ($C_4H_8O$ or butyraldehyde), 2-methylpropene($C_4H_8$ or isobutene or i-butene), 2-octenal, 2-nonenal, 2-heptenal, 2-hexenal, 2,4-decadienal, and 2,4-nonadienal. Other volatile potential markers include methyl 2,3-dihydroindene ($C_{10}H_{12}$), dimethylnaphthalene ($C_{12}H_{12}$), alkylbenzene ($C_{15}H_{24}$), n-propylheptane ($C_{10}H_{22}$), n-octadecane ($C_{18}H_{38}$), n-nonadecane ($C_{19}H_{40}$), hexadiene ($C_6H_{10}$), cresol ($C_7H_8O$), sabinene ($C_{10}H_{16}$), methyl heptanol ($C_8H_{18}O$), methyl ethyl pentanol ($C_8H_{18}O$), trimethylpentanol ($C_8H_{18}O$ or ethylhexanol or isooctanol), decanol ($C_{10}H_{22}O$), dodecanol ($C_{12}H_{26}O$), and alkyl dioxolane ($C_6H_{12}O_2$). "Non-volatile" markers would include oxaloacetic acid, acetyl CoA, acetoacetic acid, beta-hydroxybutyric acid, CML, CMhL, pentosidine, lipid hydroperoxide (LOOH), and a number of aldehydes such as MDA, 4-hydroxynonenal (HNE), 4-hydroxyhexenal (HHE), and many others. Again non-volatile markers do have some vapor pressures and thus would be detectable if the detector is sensitive enough. The use of multiple markers not only will help generate more reliable signatures to more accurateley reflect the glucose levels, but some of these markers such as pentane and acetone could contribute to better management of diabetes.

B. Detectors—Artificial Olfactory System

The sensor system design is derived from highly natural biological odor-detecting systems. Human beings and other mammals identify odors through the stimulation of olfactory cells within the olfactory epithelium. The signals thus generated are transmitted into the brain through about ten thousand secondary neurons and nerve fibers. The biological olfactory system has several important characteristics. They are:

1. There are ~100 million olfactory cells or ~1 billion odorant receptors, but
2. there are only ~1,000 different types of olfactory cells.
3. The identification of an odor is not through a specific receptor or a specific type of receptor but through the combined responses of many or all of the receptors. In effect, each type of sensor responds broadly to a range of odors rather than to a specific one. Of course, this is the opposite to a conventional gas sensor, which responds to only one gas, e.g. chlorine, and provides a unique single output.
4. Identification of the odor is through pattern recognition is the olfactory bulb and subsequent neural processing in the brain. The neural system performs effective identification possibly through matching to learned or genetically-coded patterns. It may be intended to minimize the possibility of incorrect identification and thus false alarms. This is an extremely important function, because a false positive identification may mean that a deer is running for its life because it believes that it detects the odor of a lion nearby. This kind of false alarm will unnecessarily consume energy and stress the biological system. In addition, the biological signal-processing system removes drift and is speculated to enhance the overall sensitivity of the system by three odors of magnitude.
5. The entire system is highly compact and consumes extremely low power. (In terms of intelligent information processing, the brain is by far the most efficient computational system in the world.)

Given that the human olfactory system has 100 million olfactory cells (50 million per nostril) and that each cell has ten or more cilia, each with an odor receptor, thus there are a total of 1,000 million or one billion odor receptors. But since there are only about 1000 types of olfactory receptors, there are thus approximately one million identical odor receptors of each type. This high degree of redundancy could provide an improved signal to noise ratio, and thus the biological olfactory system can provide one part in $10^{12}$ to one part in $10^{16}$ sensitivity which is more than adequate to detect the many markers stated previously.

The artificial olfactory system described in co-pending application Ser. No. 09/223,831 can "reproduce" or simulate this same set of characteristics outlined above by creating many identical "receptors" or sensing elements for each type of sensor in an artificial sensor array. Assuming that each sensing element occupies a certain amount of area, then one way to have many redundant "olfactory receptors" is to increase the detection area substantially. Making use of an aerogel, a foam-like substance that has an immensely large surface area, one can equivalently "creates" a great many sensing elements that parallel the billions of sensor cells in the biological olfactory system. Aerogel technology has demonstrated an increase in the surface area by as much as forty-thousand-fold. Aerogel material is so light and has such a large surface area that a specimen of a certain aerogel that weighs only 1 gram can have a surface area equal to that of 2.6 basketball courts. Making use of such innovative materials is one of the key aspects of the bionic olfactory system.

As indicated earlier, many different types of olfactory cells or types of sensors are needed to respond to the many different types of odors will be needed, and these sensors will have to be "coupled to" the odor molecules. The chemical nature of many of the odorant molecules points to the use of polymers, since the charges of parts of the polar molecule can act as "handles" that polymers could be "turned" to specifically attach to. In addition, different molecules will have different solubilities in these polymers; and the amount of swelling will also be different. These three different effects enhance the chemical diversity and thus allow detection of a broad range of smells as in the case of a biological nose. There are many different variants or types of polymers to choose from, thus allowing the creation of the many types of sensors needed to make an artificial olfactory system. Thus, the second major feature of the electronic nose described in co-pending application Ser. No. 09/223,831 is the use of different types of polymers on the aerogels to form different types of sensors. These polymers consist of various stationary-phase materials which are already known from gas chromatography, with most of them based on, though not restricted to, modified polysiloxanes and polyetherurethanes. For example, by using poly(3-aminopropyltrimethoxysilane propyltrimethoxysilane copolymer) of PAPPS, one can detect between 10 ppt to 1 ppb of carbon dioxide, depending on a number of relevant associated parameters. This indicates the ultra-sensitivity achievable by the sensors.

Figure 4:
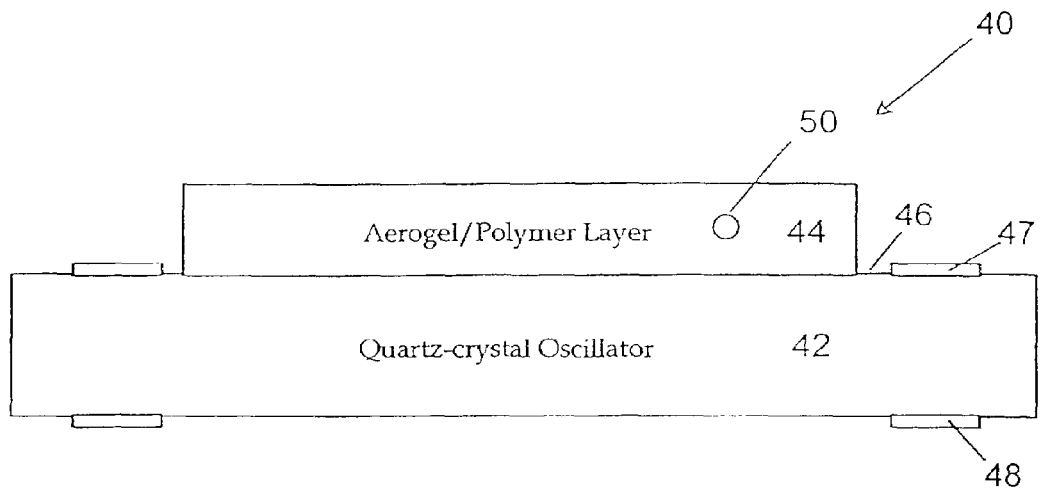
FIG. 4 is a cross-sectional view of a piezoelectric sensor.
Figure 5:
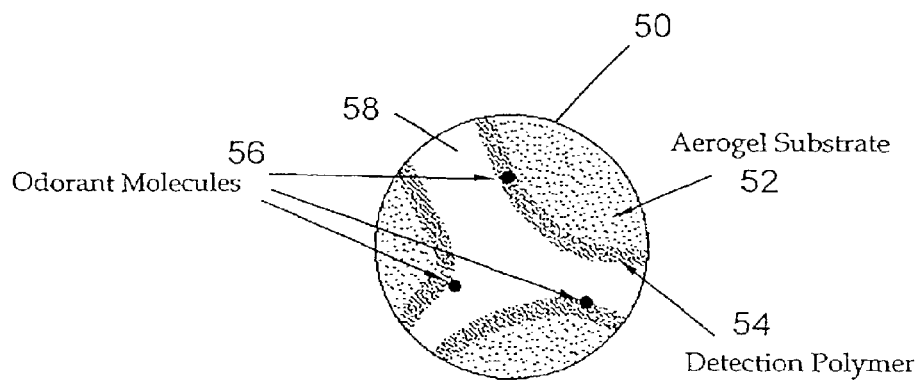
FIG. 5 is a cross-sectional view of the polymer/aerogel layer of FIG. 4.

The remaining question is how to measure the amount of the attached odorant molecules. One way is to measure the frequency shift due to the added mass when odorant molecules are coupled onto a polymer-coated aerogel which sits on top of a piezoelectric (quartz) crystal. Using phase/frequency properties of the quartz crystal, measurements can detect extremely minute crystal frequency shifts (0.0055 Hz out of 6 MHz or 1 part per billion) that occur when odorant molecules are attached. This ultra-sensitive conversion of attached odorant molecules into measurable electric signals represents the third party of the co-pending application Ser. No. 09/223,831. FIGS. 4 and 5 show the cross sections of the piezoelectric sensor and a magnified section of the polymer/aerogel layers. As shown in FIG. 4, a sensor element 40 is formed from a piezoelectric (PZ) crystal oscillator 42 having an aerogel/polymer layer 44 on a surface 46. A pair of electrodes 47, 48 on opposed surfaces of PZ crystal 42 are used to apply a voltage across the crystal to induce oscillation. Layer 44 provides a high surface area and the ability to capture odorant molecules. The sensor unit can be greatly reduced in size by using surface acoustic wave (SAW) or similar devices such as micro-machined quartz crystal unit or other miniaturized resonators without affecting the claims of this invention. A region 50 is shown in greater detail in FIG. 5. Aerogel substrate 52 has a thin coating of detection polymer 54 thereon. Odorant molecules 56 penetrate void spaces 58 in the aerogel substrate 52. Changes in the resonant frequency of oscillator 42 produced by different odorant molecules are detected.

Emulating the biological nose, the artificial olfactory system will have numerous sensors, each with a different type of polymer responding differently to various odorant molecules. Thus, the aerogel provides a very large surface area for coating of the polymer, and effectively simulates the huge number of same-type biological olfactory cells and their combined response. The polymer provides the necessary electronic and chemical coupling. And the piezoelectric crystal allows the quantitative conversion of trace amounts of odorant molecules to frequency-shift signals. Such an ultra-sensitive system is the basis of the detector for the markers of diabetes or for other markers applicable for other applications. Furthermore, a heater will be incorporated with the detector to "refresh" the system so to provide confirmation of the detection of a targeted substance. This particular feature can be important for minimizing false positive alarms, thus improving the general reliability of the system.

The use of olfactory systems to detect the markers offers a totally different paradigm for detection when compared with other traditional techniques such as HPLC and GC. Whereas the traditional techniques treat each marker as a separate entity and thus detect each marker individually, the olfactory system treats a set or a collection of markers corresponding to a condition as a pattern. As a result, the olfactory system puts the emphasis on the collective pattern rather than on each individual result. Thus the sensors corresponding to the markers in the olfactory system do not need to be as "precise" as in the case of detecting each individual marker separately. As long as the collective response in the form of a pattern is unique to a particular condition, then the neural network system or other intelligent system will recognize the signature from this collective response for that particular condition. As a result, the selectivity of detection can be much less than demanding, resulting in less stringent requirements for each individual sensor. For example, several or even all of the sensors can respond to the same substance as long as they respond differently. Thus a biological or a biological-mimicking system shifts the demand from the sensors to the signal processing unit to compensate for "inferior" sensing. This is very important because computational cost is very low whereas sensor cost is typically high. Thus this shift should could enable the design of low-cost sensing devices for many diverse applications. That is one important reason to favor using an artificial olfactory system.

Alternatively, this ultra-sensitive sensor, though it is a fundamental unit for an artificial olfactory system, can also be used as a detector in any GC or similar system, for this ultra-sensitivity would significantly boost the performance of such devices. Furthermore, a miniaturized gas chromatography capillary tube could be fabricated either by a semiconductor etching process or by using technology such as the nanotube. Thus such an ultra-sensitive micro-system can also be made very portable, somewhat resembling the artificial olfactory system. These miniaturized systems could function somewhat like chemical "integrated circuits" or CICs that process chemical signals instead of electronic signals in a miniaturized fashion. However, all CICs need ultra-sensitive detectors such as the detector in the artificial olfactory system, since the amount of chemicals is small, due to the great reduction in system size.

Even though the artificial olfactory system is a preferred way to implement the sensors for this invention, it is not the only way. This invention would also work well with other types of sensors such as GC, HPLC, or mass spectrometry. For example, in the case of GC once the retention times corresponding to the markers of this invention for diabetes are known, one can use the response signals that correspond to these time locations to obtain a signature for the breath. The resulting signature will be treated in the same way as that obtained from the sensors in the artificial olfactory system. Similar considerations apply to other devices.

Besides these established systems, the present invention can also apply to other types of detectors such as certain conducting nanotubes whose conductivity changes as a result of gas absorption. Such a device, similar to the piezoelectric-based sensor, can be the building unit for an artificial olfactory system. Thus the invention is broadly applicable to many different types of sensors fabricated from many different technologies, and is not restricted to the artificial olfactory system described here.

C. Signal Processing—Neural Networks and Fuzzy Filters

Signal processing for pattern recognition that mimics the brain to distinguish different odors and the quantification of the intensity of each detected odor will be done by artificial fuzzy neural network circuitry. The main reason is that the production and metabolism of volatile markers can be different from individual to individual, and thus an adaptive algorithm is needed to adapt an individual's markers' deviations from his/her norm to correlate with his/her status or condition as represented by some detected markers. Since the body is so vastly complex, deriving formula from first principles to describe such relationships is virtually impossible.

An illustration of the flexibility of the invention is glucose measurements for diabetes when glucose itself is not measured but a number (X) of secondary markers are measured. An empirical and direct way to "translate" the markers' levels to glucose levels is to use a neural network or similar device. Corresponding to each glucose level for an individual is a set of values for the X volatile secondary markers obtained from the individual, assuming that one establishes ahead of time that X markers are required to characterize the glucose level. For a different glucose level for the same individual, some or all of these X markers will be of different values. Thus, this is a pattern recognition problem. Each set of values for these X markers will provide a pattern or a signature that is unique to a particular glucose level for that particular individual. A neural network with fuzzy filters will then be used to map these signatures to the different glucose levels for that individual. For another individual, the neural network that describes his/her mapping will probably be different.

Pattern recognition using neural networks is a well-established art and is well suited for the individual adaptation algorithm. Neural networks also offer three very unique advantages. They can be made relatively immune to noise, especially by injecting noise into the data during training. Secondly, once the neural network has been trained with a limited but adequate amount of data, it can adapt or learn the underlying fundamental relationship between the inputs and the outputs to provide appropriate outputs even when presented with a set of inputs that it has not been trained on before. This is possible because of the neural network's ability to generalize or to learn. Furthermore, when more input and output data pairs are presented to the neural network as time goes by, it will get more and more accurate and/or adapt to the body that may be changing, such as might be the case of normal aging. Finally, a neural network modeled after its biological counterpart is a distributed computational system and thus will not fail catastrophically if some of its neurons or synapses are damaged. The system will typically degrade gracefully or gradually as more and more neurons or synapses die. This robustness is essential for vital applications such as medical ones.

Figure 6:
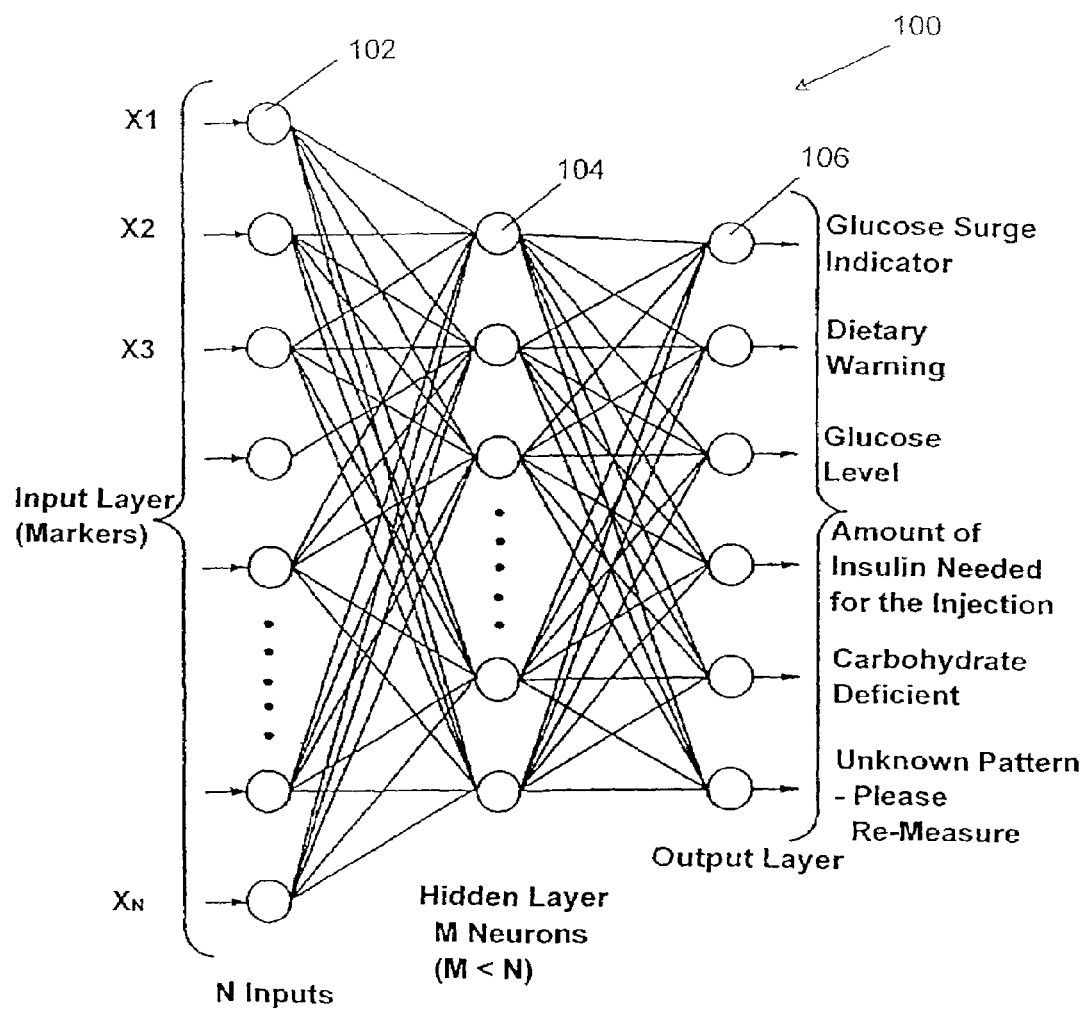
FIG. 6 shows an artificial neural network (ANN) for adaptive pattern recognition.

To implement such a neural network for the application of glucose measurement, assuming that 20 markers are needed for such characterization, will require a neural network with 20 inputs in the input layer. If glucose is the only desirable output, only one neuron is needed in the output layer. However, since the markers provide a rich set of metabolic information, glucose would not be the only desirable information, and there would likely be more output neurons. For example, some of these markers could also be used to monitor certain dietary habits, and thus provides a dietary warning output; whereas some of these markers collectively can be used as a predictor for a glucose surge even before the actual glucose rise. For most applications, such empirical modeling can typically be achieved with a three-layer neural network. The number of neurons for the middle or hidden layer would typically, though not always, be a number intermediate between the number of neurons in the output layer and the number of inputs in the input layer. In this example, typically the middle layer will have one to twenty neurons. To a first order of approximation, the number of neurons in this layer is governed by the number of features in the patterns presented to the network. For the purpose of better generalization, one typically constrains the number of neurons in the hidden layer to a minimum. This constraint forces the system to fit all data with a minimal number of "fudge" parameters, resulting in a model that could describe the underlying fundamental characteristics. FIG. 6 shows a three-layer artificial-neural-network (ANN) implementation of the signal processing system. ANN 200 has N input neurons 102 at which the measured markers are inputs. The N input neurons 102 are connected to M hidden second-layer neurons 104, whereby typically M is less than N. The hidden layer neurons 104 are connected to K output neurons 106, e.g., K=6, corresponding to various conditions determined by the ANN 200 from the input markers.

Figure 7:
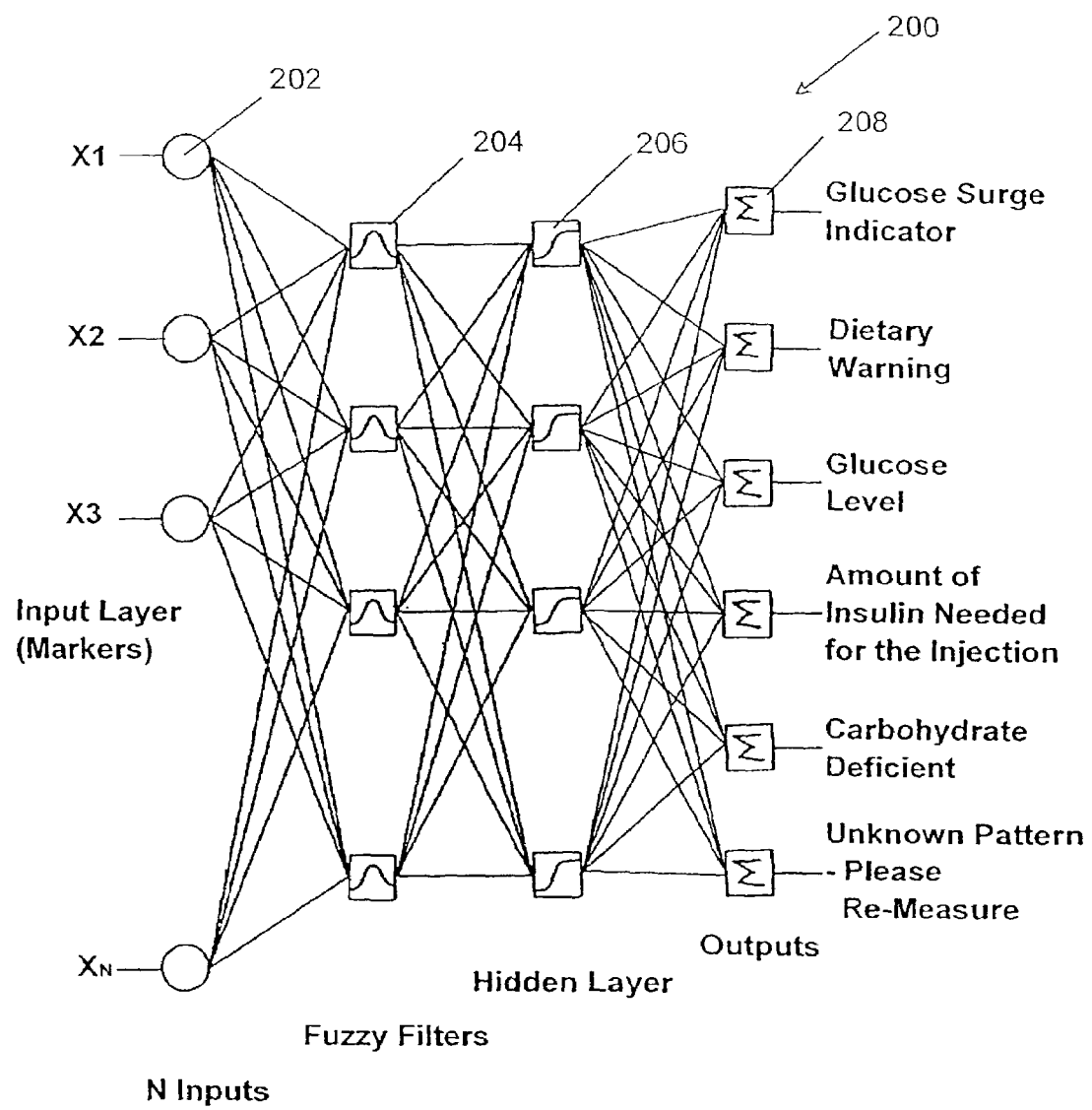
FIG. 7 shows fuzzy filters in an artificial-neural-network/fuzzy-filter system for automatic selection of the appropriate input markers.

For actual implementation, such constraints in the use of neurons can be achieved by a fuzzy logic/neural network system. U.S. Pat. No. 5,664,066 describes a fuzzy/neural system with fuzzy filters at the input layer that self-adjusts to find the most relevant input channels in the input layer, given a best upper-bound guess on the number from the onset. Such a system has been proven to be valuable in handling a large number of inputs, and was able to select only the relevant inputs and thus greatly reduce the number of inputs and the corresponding synapses in the case of describing a plasma discharge. Similarly, such a fuzzy logic/neural network system, as shown in FIG. 7, can be used if there are too many potential markers because such a system will select only the most relevant markers for an application. One has to remember that the smaller the number of markers used, the lower will be the cost of the system. In addition, a system that can be fully described with a minimal number of inputs will be more fundamental and thus would also be more capable of generalization. FIG. 7 shows a four-layer artificial-neural-network/fuzzy filter (ANNFF) implementation of the signal processing system. ANNFF 200 again has N input neurons 202 at which the measured markers are inputs. The N input neurons 202 are connected to M hidden second-layer fuzzy filters 204, where typically M is less than N. The hidden layer fuzzy filters 204 are connected to L third-layer neurons 206. Finally the L third-layer hidden neurons 206 are connected to the K output neurons 208 again corresponding to various conditions determined by the ANNFF 200 from the input markers.

Figure 8:
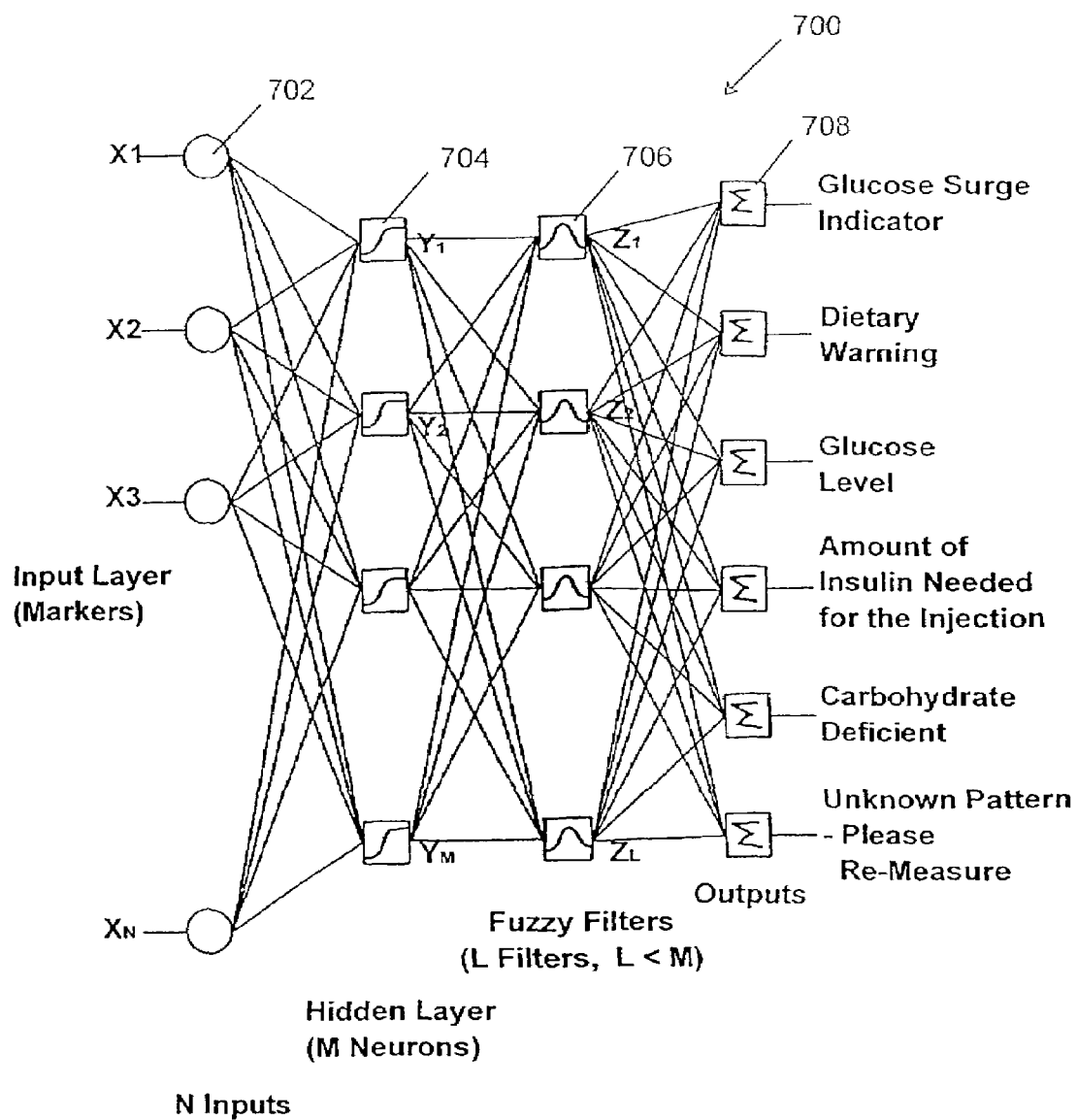
FIG. 8 shows fuzzy filters in an artificial-neural-network/fuzzy-filter system for automatic selection of the correct number of neurons in the hidden layer.

In the fuzzy/neural system according to the present invention, the fuzzy filter is positioned not at the input layer but at the hidden layer, as shown in FIG. 8, to automatically constrain the number of neurons in the hidden layer. At present, there is no theory to decide on the appropriate number of neurons in the hidden layer and thus choosing the number is a guessing game. Again, with fewer neurons and synapses, the system will be more capable of learning. FIG. 8 shows the topology of an artificial neural network/fuzzy filter 700 which incorporates fuzzy filtering in the hidden level. It includes N input neurons 702, M second-level neurons 704, L third-level fuzzy filters 706, and K output neurons 708. For a diabetic monitoring application, there may be 19 input neurons 702, 19 second-level neurons 704, 19 or fewer third-level fuzzy filters 706, and five output neurons 708.

Each node (referring collectively to all neurons and fuzzy filters) in the network of FIG. 8 performs a particular function (a "node function") based on the incoming signals and a set of parameters pertaining to the node. All the nodes in a given layer in this embodiment have the same type of node function. In particular, the nodes of layer one may simply by isolation buffers. Each of the nodes 706 (fuzzy fillers) in layer three is associated with a parameterized bell-shaped membership function given as:

$$u_j(i) = \frac{1}{1 + \left[\left(\frac{i - c_j}{a_j}\right)^2\right]^{b_j}},$$

where i is the second layer neuron number, j is the number of the particular third-level fuzzy filter 706, and the adjustable parameters are $a_j$, $b_j$ and $c_j$. The output signal from each of the i'th one of the second-level neurons 704 is therefore weighted by the function $u_j(i)$ in its connection to the j'th one of the third-level fuzzy filters 706. Each j'th one of the third-level fuzzy filters 706 then sums its weighted input values and divides by a normalization factor to produce an output signal. The output of each third level fuzzy filter 706 is accordingly given by:

$$\frac{\sum_i u_j(i) y_i}{\sum_i u_j(i)},$$

this can be rewritten as $$z_j = f\left(\sum_{i=1}^{M} w_j(i) y_i\right),$$

where f(any input)=1, M is the number of second-level neurons, the function $w_j(i)$ is defined as $$w_j(i) = \frac{u_j(i)}{U_j},$$

and the normalization factor $U_j$ is defined as $$U_j = \sum_{i=1}^{M} u_j(i)$$

The initial values of the parameters are set in such a way that the membership functions satisfy "$\epsilon$ completeness" (with $\epsilon$=0.5, for example), "normality" and "convexity". See "Introduction to Fuzzy Arithmetic: Theory and Applications", Arnold Kaufmann and Madan M. Gupta, Van Nostrand Reinhold Co., 1985, and "Fuzzy Logic in Control Systems: Fuzzy Logic Controller", C. C. Lee, IEEE Trans. on Systems, Man, and Cybernetics, 20(2):404–435, 1990. Although these initial membership functions are set heuristically and subjectively, they do not provide an easy interpretation parallel to human thinking. The parameters are later turned with backpropagation in the learning process based on the training data set. Better initial weightings can be designed by using the Central Limit Theorem to prevent saturation of the neural network.

The second layer neurons 704 perform as a hidden layer as in a standard neural network, taking weighted sums of the first-level neuron outputs and producing the transformed output through a sigmoidal function. The fourth-level output neurons 708 are similar except for the omission of the transfer function because the output values are prescaled.

Note that with given values of the membership function parameters for third-level fuzzy filters 706, and P training data, P linear equations can be derived in terms of the parameters in the fourth-level 708. These equations can be solved computationally by using the Kalman filter algorithm as described in "Fuzzy modeling based on generalized neural networks and fuzzy clustering objective functions", Chuen-Tsai Sun and Jyh-Shing Jang, in "Proceedings of the 30th IEEE Conference on Decision and Control", 1991. This technique can accelerate the learning process where learning is accomplished by computer simulation.

It can be seen that the use of a fuzzy filtering mechanism as shown in FIG. 8 could simplify the neural network architecture because fewer system parameters might need to be adjusted. In particular, in the architecture of FIG. 8, three parameters ($a_j$, $b_j$ and $c_j$) need to be adjusted for each of the L third-level fuzzy filters 706, in addition to N input weighting adjustments for each of the M second-level neurons 704, and L input weighting adjustments for each of the five output neurons 708. This benefits learning efficiency, and at the same time provides a means to automatically decide on the right number of neurons needed for the second layer.

Figure 9:
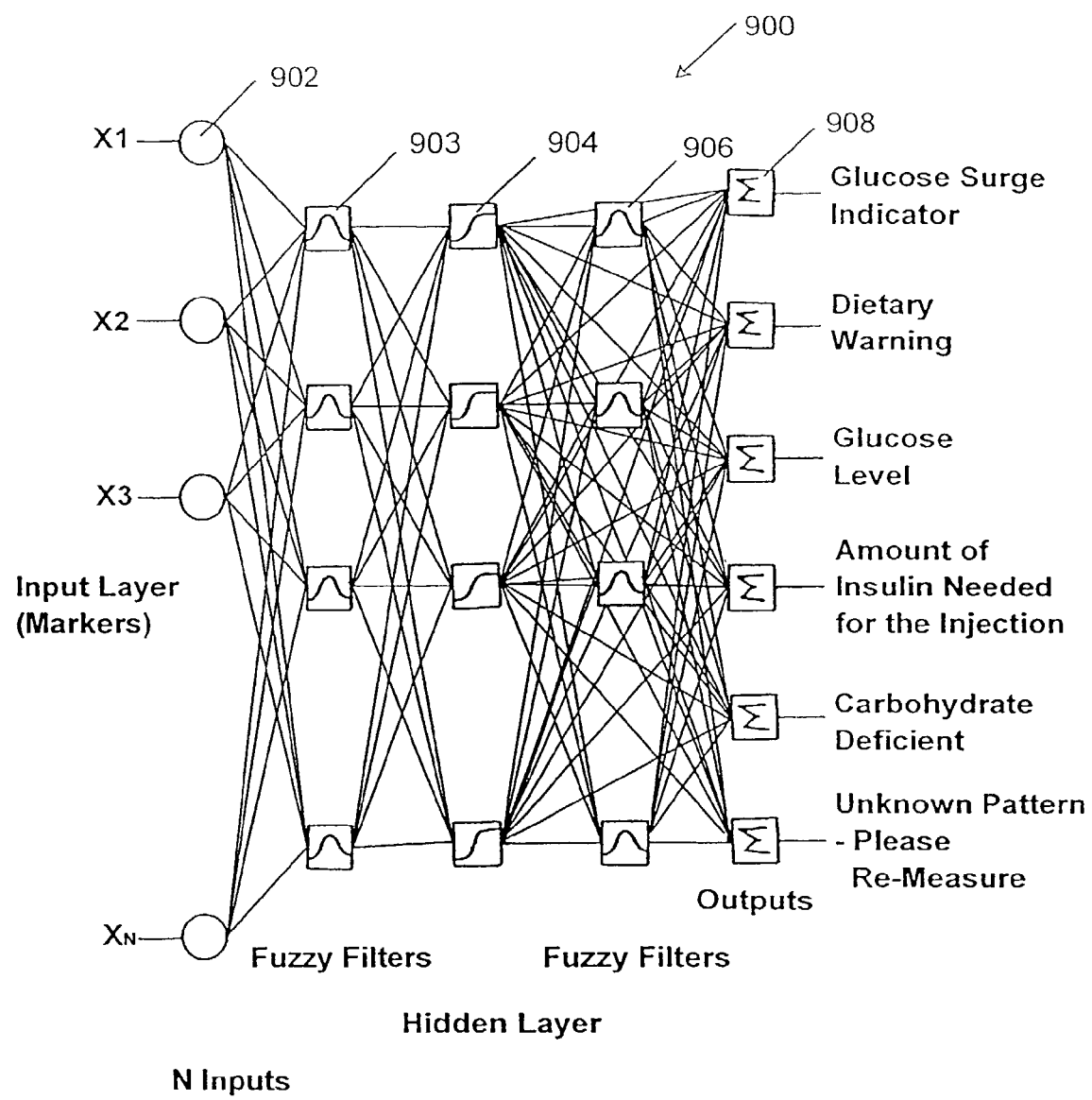
FIG. 9 shows two layers of fuzzy filters in an artificial-neural-network/fuzzy-filter system for automatic selection of the appropriate input markers and the correct number of neurons in the hidden layer.

Finally, both concepts can be combined as shown in FIG. 9, using fuzzy filters at the input to constrain the number of markers needed and using fuzzy filters between the hidden layer and the output layer to automatically choose the appropriate number of neurons in the hidden layer. FIG. 9 shows a five-layer artificial-neural-network/fuzzy filter (ANNFF) implementation of the signal processing system. ANNFF 900 again has N input neurons 902 at which the measured markers are inputs. The N input neurons 902 are connected to M hidden second-layer fuzzy filters 903, where typically M is less than N. The hidden layer fuzzy filter 903 are connected to L third-layer neurons 904. And the L third-layer hidden neurons 904 are connected to K fourth-layer fuzzy filters 906 which are finally connected to the output neurons 908 again corresponding to various conditions determined by the ANNFF 900 from the input markers.

Figure 10:
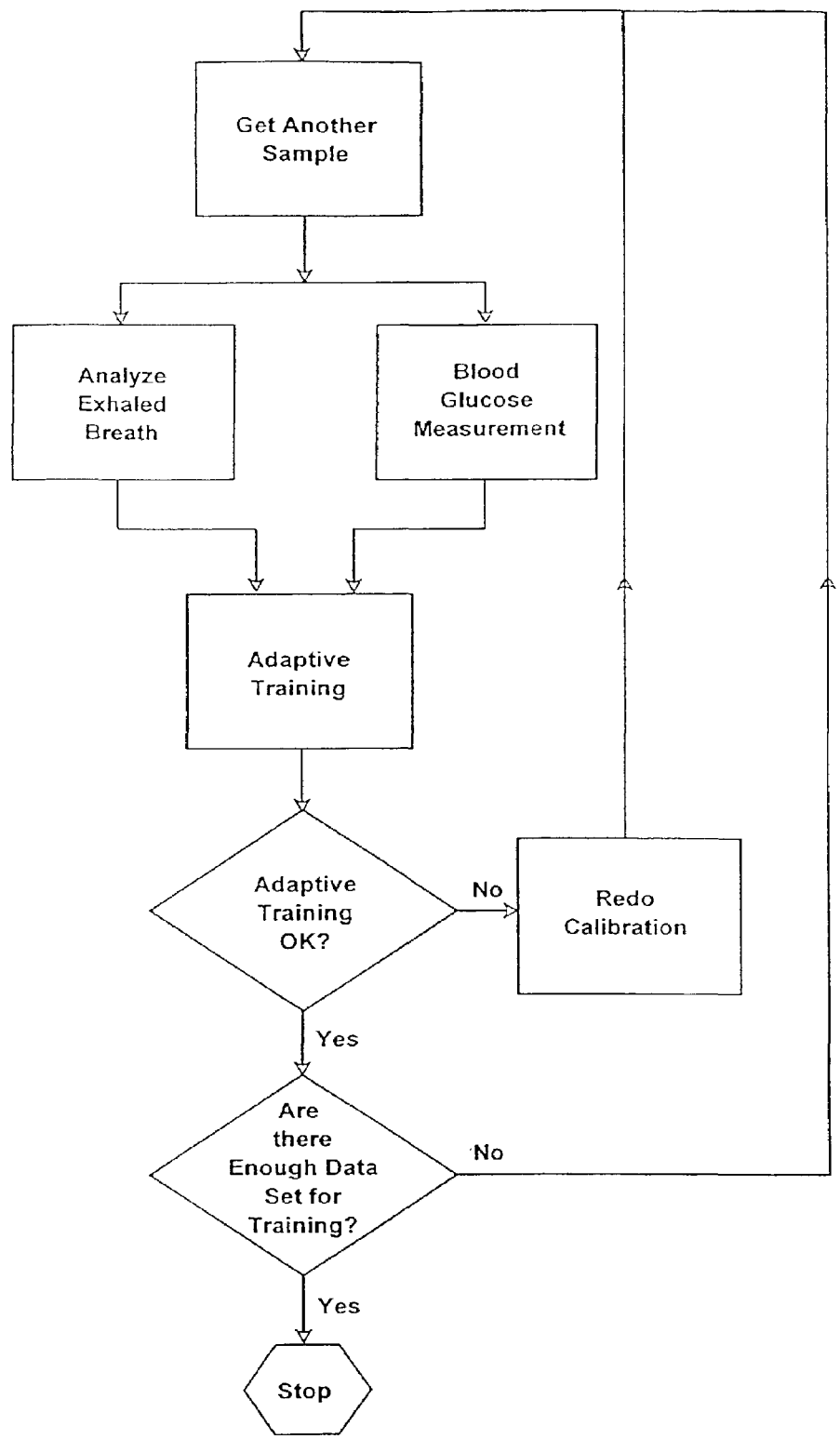
FIG. 10 is a flow chart for system calibration.
Figure 11:
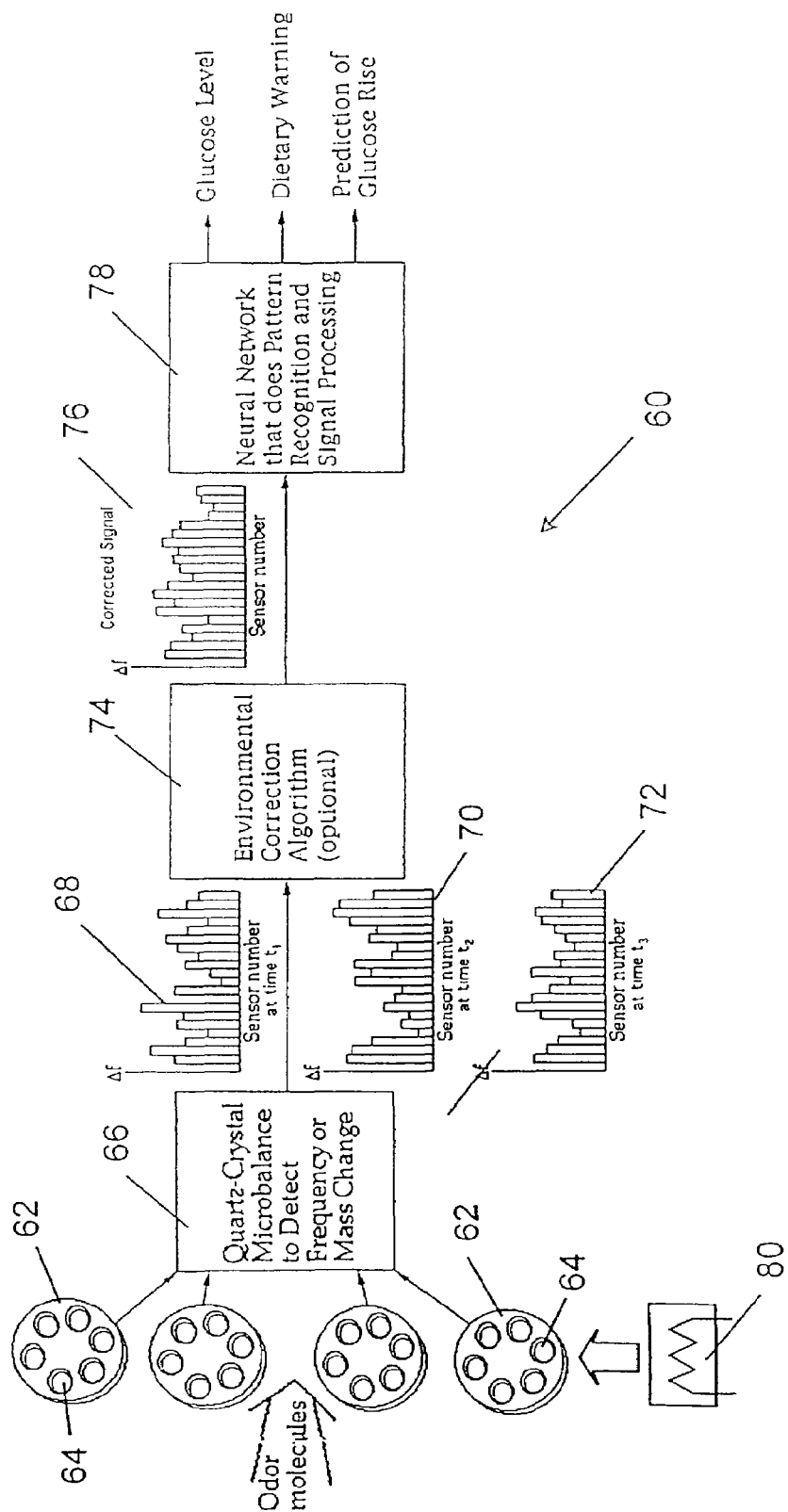
FIG. 11 shows a system diagram of the artificial olfactory-neural network apparatus.
Figure 12:
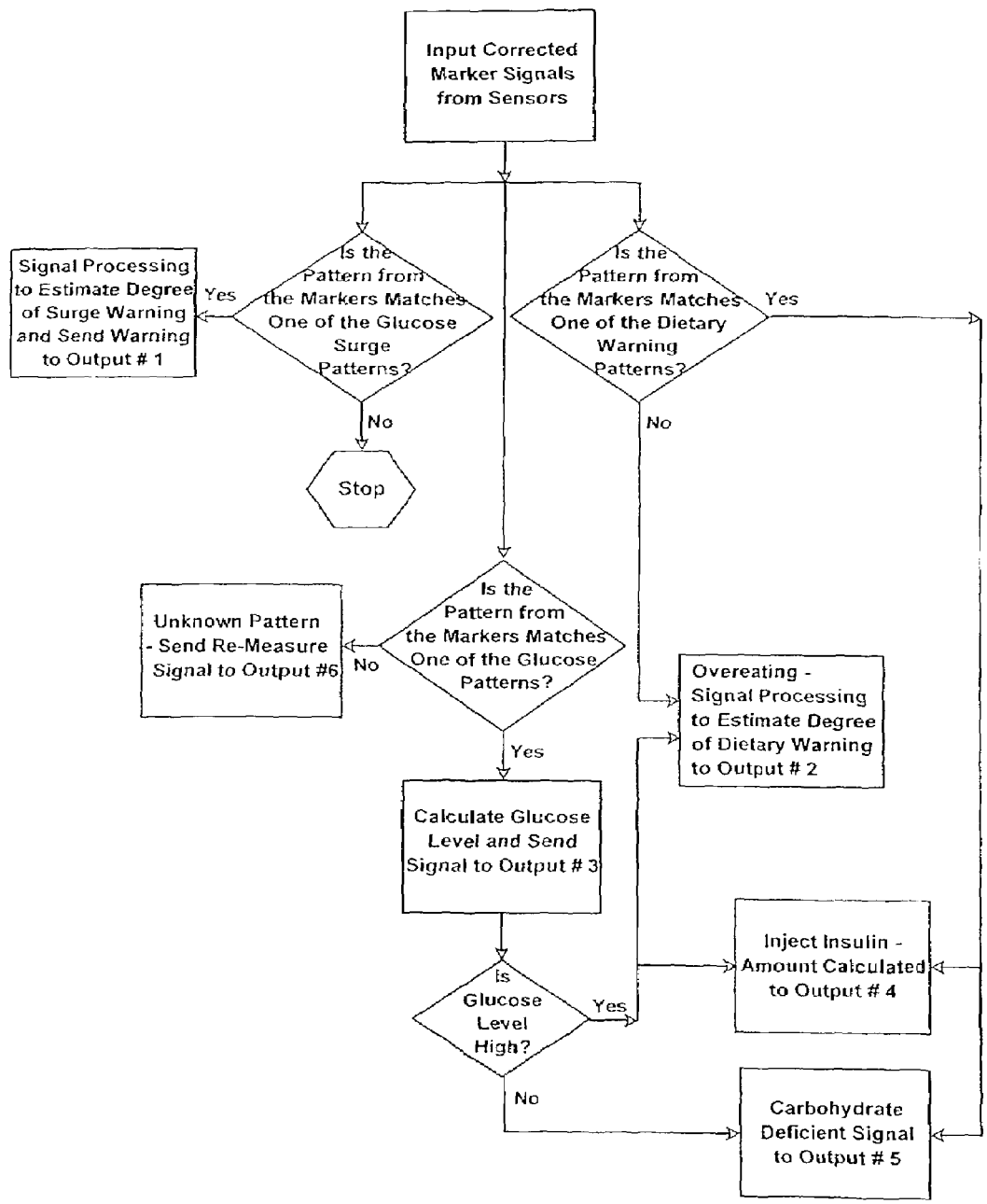
FIG. 12 is a flow chart for processing the marker signals.

The system will have to be calibrated or "trained" with each individual patient before it can be used. Before such a system can be deployed for non-invasive measurements of glucose, the patients have to provide a group of known input-output pairs to the intelligent system (such as neural networks or fuzzy/neural systems or similar intelligent systems) for training. This implies that during the calibration or training procedure, before deployment for actual measurements, every time that a glucose measurement is to be made, a breath test or a correct breath test (if the environment is polluted too much with any of the desired markers) has to be performed to provide the system with input values for training. The procedure for correcting the environmental effect has been explained earlier. The glucose level could be obtained conventionally, e.g. by drawing blood for a blood glucose measurement. The value thus found would be used as the output value to be paired with the input markers' values found through simultaneous breath measurements. These two sets of measurements form a single training vector and obviously have to be performed within a reasonable elapsed time span, such as within a few minutes, so that the breath markers and the glucose value correspond to the same diabetic condition or status. In addition, the conventional glucose measurement equipment has to be carefully calibrated so that the glucose level measured is accurate. Such input-output pairs would then be entered into the neural system as training vectors for the intelligent signal processing system to learn. The procedure would then be repeated with many more additional input-output pairs representing different glucose levels to provide more training vectors, until the intelligent system correctly learns the input-output relationship. FIG. 10 shows a flow chart describing this calibration process. From that time onwards, no further calibration or learning procedure wold be needed, and thus there will be nor more need for drawing blood samples to measure the glucose level, except for occasional calibrations to account for changes in the calibration or long-term, aging-induced modifications. The entire system for odor or gas sensing, including environmental corrections and adaptive intelligent signal processing, is shown in FIG. 11. As shown in FIG. 11, artificial olfactory system 60 has a number of sensor units 62, each of which contain a plurality (e.g., 6) sensor elements 64. The outputs of the sensor elements 64 are measured by measurement device 66. The sensor units can be greatly reduced in size by using SAW or similar devices such as micro-machined quartz crystal unit or other miniaturized resonators instead of bulky quartz crystal units. Device 66 is a frequency measurement unit, e.g., a quartz crystal microbalance, to detect frequency or mass change. Measurement device 66 produces signatures 68, 70, and 72 at adjacent short time steps. These plurality (e.g., 3) of signatures are inputs to an optical environmental correction processor 74 to produce a corrected signature 76 that is fed into an adaptive intelligent signature pattern recognition system 78, e.g., an artificial neural network or an artificial neural network/fuzzy filter system that performs pattern recognition to detect, recognize and identify the conditions of the diabetic patients. Device 80 is a heater used to refresh the system to improve reliability. FIG. 12 shows a flow chart describing the intelligent information processing to provide appropriate outputs to a patient in the case of diabetic monitoring.

D. Other Applications

1. Cancers

Flexibility is one of the most important advantages of this invention, the application of this invention to glucose measurement has been extensively discussed, the applications of this device can go beyond diabetic monitoring. One such application would be in the area of cancer. Since oxidative stress and lipid peroxidation markers have been described in detail above, these findings can be leveraged upon because oxidative stress and lipid peroxidation are vital to other ailments such as breast and colon cancers. The multistep carcinogenic process is regulated by the interaction between pro- and anti-oxidants. Experimental studies have revealed that a pro-oxidative stage is related to promotional stimuli in carcinogenesis, and antioxidants were shown to inhibit the induction of tumors.

Fat metabolism has been increasingly implicated in the possible development of cancer. Fats may act on tumor promotion and progression by being peroxidated into reactive intermediates and other growth-stimulating products. Factors initiating peroxidation include active oxygen derivatives, reactive metabolites of chemicals, or other radicals produced via peroxidation. Autoxidation may be initiated by hydroxyl or hydroperoxy-radicals and via binding of singlet oxygen and alkoxy radicals into double bonds and hydrogen abstraction caused by hydroxyl-radicals. These reactions may cause DNA damage and cell degeneration, affecting several stages of the carcinogenesis process. Furthermore, n-6 fatty acids increased experimentally-induced mammary cancer by affecting prostaglandin synthesis which was prevented by n-3 fatty acids. Thus both the quantity and quality of fat were found to modulate cancer incidence and target organs in experimental animals, and they also affect the pro-oxidant-antioxidant parameters, possibly because of the relationship between reactive radicals and autoxidation.

Many epidemiologcal studies have shown an association between fat intake, and breast and colon cancer incidence and mortality. The incidence of breast cancers is closely related in countries where consumption of fat is the highest. In Japan, nationwide dietary changes during the last 30 years in the fat intake, from less than 10% energy level to the present 25% level, have also been followed by a concomitant increase in mortality also from breast and colon cancer.

Peroxidation of different PUFAs can result in the production of hydrocarbon alkanes, namely pentane and ethane. Thus a linkage of breast and colon cancers to hydrocarbons exhaled from one's breath is expected. This linkage has been reported and the increase or pentane in the breast cancer case is especially dramatic, a 400% increase when compared with age-matched controls. Thus the invention can be used as a preliminary screening tool to provide evidence to support further investigation so as to provide a definitive diagnosis of breast and colon cancers.

Many types of cancers can produce changes in breath composition. Similarly, researchers have found correlation of exhaled volatile markers in the case of lung cancer. In one research study, of the 386 components detected in the exhaled breath using gas chromatography/mass spectrometry (GC/MS), 28 components were found a >90% occurrence level for lung cancer patients. Of these 28 components, 19 components ostensibly represent environmentally-related pollutants that appear to bear little relevance to a biochemical marker. Thus the remaining 9 represent diagnostic markers. They are propenal ($C_3H_4O$), acetone ($C_3H_6O$), 2-butanone ($C_4H_8O$), phenol ($C_6H_6O$), benzaldehyde ($C_7H_6O$), acetophenone($C_8H_8O$), nonanal ($C_9H_{18}O$), ethylpropanoate ($C_5H_8O_2$), and methylisobutenoate ($C_5H_8O_2$). These markers are associated with early stages of diagnosis, but as the disease progress, one would expect additional markers because the host defense mechanism is important in the development and growth of tumors.

The complex host defense and immunological mechanism against cancer contain several types of cells, including macrophages. They can be activated both in vivo and in vitro to kill tumor cells. The oncolytic activity of macrophages is either mediated by direct macrophage-to-tumor cell contact or attributed to the production of soluble tumor cytotoxic factors, such as tumor necrosis factor-alpha (TNF-alpha), interleukin I (IL-1), IL-6, cytolytic proteases, garginases, lysosomal enzymes, prostagalandins, oxygen radicals, and reactive nitrogen species, particularly NO. The cytotoxicity of activated macrophages against tumor target cells is dependent on the synthesis of NO. The production of NO from activated macrophages destroys or prevents tumor cell division by inhibition of DNA replication and restraint of mitochondrial respiration. Thus, NO production is enhanced in patients with malignancy either directly from tumor cells or from activated macrophages as host defense mechanisms against tumor cells. There is evidence that NO may contribute to tumor control during radiotherapy and it may be involved in some of the therapeutic activities of chemotherapy by increasing nucleic acid damage and by disruption of intracellular signaling. NO also plays a fundamental role in radiation tissue injury and may be involved in some of the side-effects of chemotherapy.

The exploration of a prognostic role of NO in response to chemotherapy or radiotherapy may further elucidate the biological activities of NO in primary lung cancer. As a result, NO together with some of the oxygen radicals could be very useful markers for the assessment of later-stage lung cancer and the response to therapy. Adding these markers to the list above produces a comprehensive evaluation system that can assess the different stages of lung cancer. This would provide valuable information for treatment strategy and the in-depth patient management. These markers can also play a certain diagnostic role. For example, as a screening tool certain signatures of these markers may warrant further investigation such as one based on the enormously expensive spiral computer tomography scan which according to Dr. Barnett Kramer, deputy director of the division of cancer prevention at the cancer institute, said that it would cost $39 billion to screen all smokers and former smokers in the country.

2. HIV/AIDS

Another application for the invention is in the area of HIV. HIV infection causes a progressive impairment of immune function resulting in increased susceptibility to opportunistic infection and malignancy characteristic of HIV/AIDS. Of the mechanisms contributing to this progression, oxidative stress induced by the production of reactive oxygen species (ROS) or oxygen free radicals (OFR) may play a critical role in the stimulation of HIV replication and the development of immunodeficiency. Excessive production of ROS such as superoxide anion, hydroxyl radical, and hydrogen peroxide may be related to an increased activation of polymorphonuclear leukocytes during infections, or influenced by the pro-oxidant effect of tumor necrosis factor alpha produced by activated macrophages during the course of HIV infection. ROS can attack double bonds in PUFAs, inducing lipid peroxidation, which may result in more oxidative cellular damage. Thus measurement of lipid peroxidation or products of lipid peroxidation will help assess the degree of cellular damage. Hydrocarbons such as pentane and ethane were used for non-invasive assessments using gas chromatography equipment on 64 subjects (49 non-smoking HIV-positive patients with no active opportunistic infection and 15 age-matched seronegative controls). Breath ethane and pentane outputs for HIV subjects respectively are 28.1 and 9.05 pmol/kg/min which are significantly higher than the corresponding values of 11.42 and 6.06 pmol/kg/min for the controls. These data were further supported by the results of plasma lipid peroxide which is 50.7 micromol/L for HIV subjects vs. only 4.5 micromol/L for the controls.

The finding of increased lipid peroxidation is consistent with findings from other studies. The increase in lipid peroxidation was also associated with lower plasma concentration of antioxidant micronutrients such as vitamin C, alpha-tocopherol (vitamin E), beta-carotene, and selenium. Of these antioxidants, vitamin E is the most potent and most abundant lipophilic antioxidant in vivo as well as an immunoenhancer. Vitamin C is the major water-soluble antioxidant and acts as the first defense against ROS in whole blood and plasma. In addition, a cooperative interaction exists between the two vitamins, vitamin C being important in regenerating vitamin E during the antioxidant defense process. The antioxidant deficiency in HIV-position populations is probably due to increased utilization of antioxidant micronutrients because of increased oxidative stress rather than to inadequate dietary intake or malabsorption. Again, a weakened antioxidant defense system, in turn, could lead to further enhancement in lipid peroxidation.

These findings are significant because in in-vitro experiments, researchers have shown that ROS such as hydrogen peroxide can specifically activate the nuclear factor κB to induce the expression and replication of HIV-1 in a human T-cell line, and the addition of antioxidant vitamins blocked activation of nuclear factor κB and inhibited HIV replications. Thus the picture presented is self-consistent and lends credence to the use of non-invasive breath measurement techniques to assist monitoring the progress of HIV.

Further study on the effect of vitamin E and C supplements on oxidative stress and viral load in HIV-infected subjects provides additional support for the use of pentane as a non-invasive marker. The vitamin group (n=26) has a significant change of −2.5 pmol/kg/min in breath pentane in 3 months vs. a change of +1.9 pmol/kg/min for the placebo group (n=23). Corresponding changes in plasma lipid peroxides are −36 nmol/ml and +27.1 nmol/ml for the supplement and placebo groups, whereas the plasma log viral load showed a change of −0.45 $\log_{10}$ copies/ml for the supplement group vs. +0.5 $\log_{10}$ copies/ml for the placebo group. Thus the study showed that vitamin E and C supplementation significantly decreases oxidative stress in HIV-infected individuals, and with this supplementation there was a trend towards a reduction in viral load.

The relatively low cost of vitamin C and E may be very important in terms of public health problems in impoverished, Third-World nations. Since this investigation was done before the introduction of the combination antiretroviral therapies containing protease inhibitors, the finding is important for economic reasons. Since only about 10% of HIV-infected individuals in the world can afford such expensive therapy, this vitamin supplemental approach could have great benefits in developing countries. The results of that study may have some implications for maternal and child health, since increased oxidative stress has been associated with adverse pregnancy and birth outcomes. Furthermore, the effect of antioxidant supplementation on mother-to-infant transmission could be important, because in the study, viral load reduction was similar to that seen with zidovudine, a drug known to reduce HIV transmission from mother to infant. While vitamin supplement is very economical in comparison with the cocktail therapy, the present invention could play a vital role in low-cost monitoring of the progress and status of the HIV-infected subjects, especially in poor developing countries.

In addition to ethane and pentane as non-invasive markers for HIV-positive patients, there is reason to suspect that endogenous NO production in the respiratory tract may be reduced in HIV-infected subjects because a syndrome very similar to primary pulmonary hypertension occurs in HIV infection and endogenous NO may be reduced in some types of pulmonary hypertension. In one research study, the amount of exhaled NO from 36 HIV positive subjects was significantly less than that of 31 age-, weight-, and height-matched controls, 39 nl/min/m$^2$ vs. 57 nl/min/m$^2$. (Exhaled NO is proportional to body surface area; thus the unit here is expressed in exhaled NO per m$^2$). The possible reasons for such a reduction could be multifactorial and be due to either reduced constitutive or inducible NO syntheses function from progressive immunological deactivation or other mechanisms.

3. Mental Illnesses

Evaluation of exhaled substances may also be important in the diagnosis of mental illness. Schizophrenia is a common and devastating psychotic illness affecting approximately 1% of the population of all cultures, and often culminates in severe disability and premature death. Despite the high incidence of the illness, there is at present no laboratory test for the condition. The central thesis of the membrane hypothesis of schizophrenia is that there is an abnormality in membrane function involving the major essential fatty acids—arachidonic acid (AA) and docsahexaenoic acid (DHA). The high levels of polyunsaturated fatty acids in brain cell membranes, together with the enhanced oxygen throughput in this tissue, mean that the brain's AA and DHA are more susceptible to oxidative degradation than is the case for these acids in the membranes of other tissues. One of the possible molecular lesions in schizophrenia is an enhanced activity of brain phospholipase. The enhanced oxidative degradation of these PUFAs essentially implies high level of volatile products such as ethane and pentane resulting from cellular injuries. Pentane is found to be significantly higher in schizophrenia patients that age-matched controls. Furthermore, using pentane as an index, it was found that the elevated levels of the hydrocarbons in the patients decreased back to the normal levels with therapy. During the drug therapy, it was noted that there were periodic bursts of pentane breath levels exceeding the control levels. Both the rates of these surges and also the baseline levels before therapy correlated with severity and duration of condition and also with the pre-existing level of negative disorders. It is encouraging that the levels of ethane and pentane markers correlate with the remission of symptoms, indicating that they could have a role as an objective measurement of drug therapy. This is very important since there is no laboratory test for schizophrenia.

Furthermore, pattern recognition of the following eleven markers on breath (2-methylbutane, trichlorofluoromethane, 2-pentanol, pentane, dichloromethane, trichloroethene, benzene, 1-chloro-2-methylbutane, 2,3,3-trimethylpentane, 2,2-dimethylbutane, and tetrachloroethene) allows identification of patients of schizophrenia with a sensitivity of 80% and a specificity of 62%. In a separate research effort, increased manufacture of carbon disulfide ($CS_2$), a known neurotoxin, has been elevated substantially in comparison with controls. The toxic effects of $CS_2$ may be due to its reaction with amines or thiols; the resulting chelation of metals may inhibit the activity of dopamine beta hydroxylase and cause disturbance of cathecholamine metabolism.

With the present invention, it is expected to do better than these reported results, for the simple reason that these research studies have only made very elementary environmental corrections only. But the correction algorithms which are part of the invention are far more sophisticated and accurate by taking into account both the lung and the body (tissue/fat/muscle) reservoirs, so better performance is expected than the current reported findings. Thus a low-cost, doctor-office, diagnostic system based on the invention could be used as a pre-screening system that precedes far more expensive investigations such as in the case of lung cancer, which have to use computer tomography techniques for the final analysis.

4. Simplified Blood Test

Finally, another possibility in using the invention is in the area of blood tests. Blood tests are a vital diagnostic tool for modern medicine. However, while only some adults does not get used to the needles for blood tests, this is usually not the case for children who are typically frightened by the sight of needles. The lung is a vital organ for gas exchange. Gas is brought to one side of the blood-gas interface by airways and blood to the other side by blood vessels. By wrapping the small blood vessels (capillaries) around an enormous number of small air sacs called alveoli, the lung creates an enormous (some 50–100 square meters) surface for gas exchange. The blood-gas barrier is as thin as 0.5 micron and the gas exchange is controlled by simple diffusion through this thin barrier. This thin and large surface area provides maximum efficiency for gas passing through. As a result, if a substance in the blood has sufficient vapor pressure, it will find its way across this barrier to the other side and be brought to the outside as exhaled breath. Thus, one can essentially measure almost any substances in the blood by analyzing the exhaled breath provided that the substance has enough vapor pressure or that the detector is sensitive enough. As a result, one can virtually do a blood test without drawing blood by simply analyzing the exhaled breath. Of course not all substances will be available through the breath; for example large molecules such as those of proteins will probably be not accessible. However, many components in the blood can be measured non-invasively without pain using this breath analysis technique.

5. Health-Related Concern—*E. coli*

In addition to direct medical applications, the device could also play an indirect role in the medical arena through other health-related concerns. One such possibility is the detection of pathogens such as verocytotoxigenic *E. coli* (VTEC). Since numerous studies have implicated meat and other foods as important sources of VTEC, considerable effort has been directed toward the testing of food products for such pathogens. Current methods for detecting *E. coli* involve the use of its biochemical characteristics, such as the inability to ferment sorbitol, polymerase chain reaction (PCR) amplification and nucleic acid probes, and several types of immunoassays. Due to the low numbers of organisms present in contaminated foods, either enrichment or amplification of the target organism is required, or alternatively an ultra-sensitive detector is needed to attain the required limits of detection. Furthermore, few of these methods are efficient in terms of the time needed for analysis and the requirement for testing large numbers of samples. As the estimated prevalence of *E. coli* in meats is approximately 5%, a rapid, highly-sensitive assay technology would enable the routine screening of meat products to correctly identify the high proportion that is free of this dangerous organism. The invention offers the possibility of rapid detection at a significantly lower cost than existing methods. In order to achieve this result, advantage is taken of several known, characteristics metabolic paths of *E. coli*.

Research has revealed that one such metabolic route, known as the shikimate pathway of common aromatic pathway, leads to the production of a wide variety of aromatic compounds. This pathway starts with 3-deoxy-D-arabino-heptulosonate 7-phosphate (DAHP), going through shikimate (an intermediate compound), and then to chorismate, a compound which finally leads to two substances that could facilitate the detection of *E. coli*. One such substance is indole (2,3-benzopyrrole; ketole; 1-benzazole; benzopyrrole) with a chemical formula of $C_8H_7N$; and the other one is catechol (pyrocatechol, 1,2-benzenediol; 1,2-dihydroxy benzene) with a chemical formula of $C_6H_6O_2$. Indole has an intense fecal odor and catechol has a phenolic odor. Catechol has a relatively high vapor pressure of 10 mm Hg at 118° C. Though indole's vapor pressure is unknown, its low melting point of 52° C. implies that its vapor pressure will also be relatively high. Thus these two compounds can provide unique analytical signatures for the presence of *E. coli*.

Figure 13:
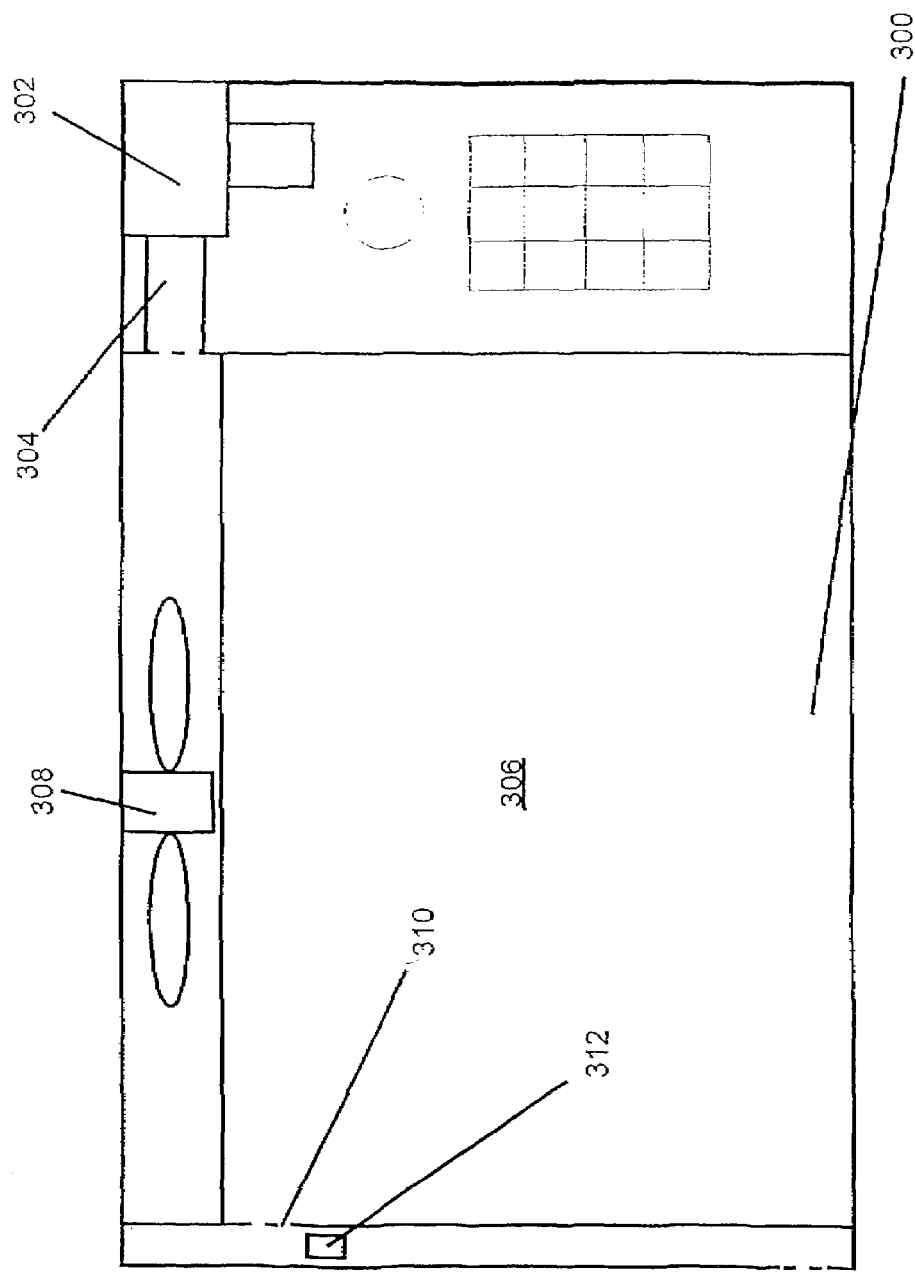
FIG. 13 shows an artificial olfactory system deployed inside a microwave oven.

Other chemical processes are also characteristic of potentially harmful bacteria. Fermentation is a vital source of energy for microorganisms. Whether or not a bacterium is a fermenter, it will probably dissimilate sugars through one of the following pathways, namely the Embden-Meyerhof pathway, the phosphoketolase or heterolactic pathway and the Entner-Doudoroff pathway. *E. coli* ferments through the Embden-Meyerhof pathway, a process that bacteria use to produce a variety of fatty acids, alcohols, and gases. Embden-Meyerhof fermentations in bacteria can lead to a wide array of end products, depending on which one of the four possible paths is taken in the reduction steps after the formation of pyruvate. *E. coli* uses the mixed acid fermentation path, which leads to the production of mixed acids and gases such as lactate, acetate, formate, succinate, and ethanol as well as $CO_2$ and $H_2$. These compounds along with the other biomarkers, indole and catechol, signatures for different strains of *E. coli* will be available for detection, provided again that the detector has enough sensitivity, since only a low number of organisms are presented in contaminated foods. Incorporating the invention into a microwave oven 300 as shown in FIG. 13 and operating it during the defrost cycle could allow detection of *E. coli* and possibly over toxic microorganisms to safeguard food intake. Microwave oven 300 has a conventional magnetron 302 connected through a waveguide 304 to input microwave into oven chamber 306 using rotating stirrer blades 308 to distribute microwave energy. When defrosting food in chamber 306, volatile markers pass through vent 310 to artificial olfactory system 312. Olfactory system 312 is shown positioned in microwave oven 300 but may be otherwise connected thereto. Under certain conditions, olfactory system 312 can be a simplified system consisting of only one or two sensors for the detection of odors from indole and/or catechol. It forms a part of the diagnostic system of the present invention.

Similarly, other pathogens such as *Salmonella, Staphylococcus aureus, Bacillus anthracis* could be detected by the same approach.

6. Health-Related Concern—*Helicobacter pylori* (or *H. pylori*)

Peptic ulcer disease is a highly prevalent disorder that has historically resulted in significant morbidy and mortality in affected persons. Recent advances on the pathogenesis of this disease have implicated infection with the bacterial species *H. pyroli*. The detection of this pathogen is significantly elevated in affected individuals, and treatment of this infection often results in cure of the ulcer disease symptoms. Current evaluation of patients with peptide ulcer disease involves serologic testing of blood for evidence of infection, and examination of expired gas for evidence of 13C and 14C species liberated by the bacterial breakdown of urea. Characteristics of this bacterium is a urease activity that results in cleavage of urea and release of breakdown products that can be detected in the breath. The proposed device would provide and alternative and less expensive diagnostic tool for the diagnosis of *H. pylori* infection, and the assessment of efficacy of treatment regimen.

7. Others

Other medical conditions or illnesses will have their own specific metabolites and thus should have their own odor characteristics. For example, Risby showed that lipid peroxidation measurement via exhaled ethane might permit sensitive and non-invasive monitoring of therapy for reperfusion injury such as myocardial and extra-myocardial reperfusion injury during cardiopulmonary bypass (CPB), or non-invasive monitoring cytotoxicity when a patient undergoes total body irradiation as might occur in the case of therapeutical treatment of leukemias and other malignancies of the hemopoietic system. Other potential uses include clinical diagnostics through breath analysis for renal failure and liver disease. Still other medical application examples include a halitosis test for stress or stomach disorders and a sweat skin smell evaluation for Hansens's disease.

Changes and modifications in the specifically described embodiments can be carried out without departing from the scope of the invention which is intended to be limited only by the scope of the appended claims.

I claim:

1. A method for determining a condition of an entity comprising:

selecting a set of volatile markers which are characteristic of a condition and which will be found in a gaseous emanation from the entity;

non-invasively detecting these volatile markers in the gaseous emanation from the entity;

processing the detected marker data in an artificial neural network that includes a fuzzy filter system.

2. The method for claim 1 further comprising further processing the detected marker data with a correction algorithm to eliminate environmental contributions to the markers.

3. The method of claim 1 wherein the volatile markers are detected using an artificial olfactory system.

4. The method of claim 1 wherein the detected marker data is processed with an algorithm which intelligently adapts to an individual entity.

5. The method of claim 1 wherein the entity is selected from the group consisting of living humans, other living animals or organisms, and non-living entities.

6. The method of claim 5 wherein the entity is a living human and the volatile markers are characteristic of a disease or other medical condition.

7. The method of claim 6 wherein the disease is selected from the group consisting of diabetes, cancer, mental illness,, ulcers, and HIV.

8. The method of claim 5 wherein the entity is food and the volatile markers are characteristic of food degradation.

9. The method of claim 1 wherein the markers are selected from supermarkers which correlate substantially with a single condition, and collective supermarkers which comprise of a set of secondary markers which individually correspond to more than one condition but collectively correspond to a single condition.

10. A method for determining a disease or other medical condition of a person comprising:

selecting a set of volatile markers which are characteristic of the disease or other medical condition and which will be found in the exhaled breath or other gaseous emanation from the person;

non-invasively detecting these volatile markers in the exhaled breath or other gaseous emanation from the person;

processing the detected marker data in an artificial neural network that includes a fuzzy filter system.

11. The method of claim 10 wherein the volatile markers are detected using an artificial olfactory.

12. The method of claim 11 wherein the detected marker data is processed with an algorithm adapted to an individual person by training the neural network with calibration data from the person.

13. The method of claim 10 further comprising further processing the detected marker data with a correction algorithm to eliminate environmental contributions to the markers.

14. The method of claim 13 wherein the environmental correction of detected markers is performed by fitting a minimum of three measured points to a pre-established wash-out curve for each marker.

15. The method of claim 10 wherein the disease is diabetes and the markers are selected to measure the destruction or deterioration of islet cells.

16. The method of claim 10 wherein the disease is diabetes and the markers are selected to measure the destruction or deterioration of cell membranes by lipid peroxidation or protein oxidation.

17. The method of claim 16 wherein the markers are used to predict a rise in glucose preceding the actual rise in glucose.

18. The method of claim 16 wherein the cell membranes are erythrocyte cell membranes.

19. The method of claim 15 wherein the markers are used to detect an overeating condition.

20. The method of claim 16 wherein the markers are selected from the group consisting of: carbon dioxide ($CO_2$), acetone ($CH_3COCH_3$), hydrogen peroxide ($H_2O_2$), ethane ($C_2H_6$), ethanol, pentane ($C_5H_{12}$ or methylbutane), pentanol, isoprene ($C_5H_8$, 2-methylbuta-1,3-diene), hexanal ($C_6H_{12}O$ or caproaldehyde or n-capric aldehyde), propanol ($C_3H_6O$ or propional or propionaldehyde), pentanal ($C_5H_{10}O$ or valeral or valeraldehyde), butanal ($C_4H_8O$ or butyraldehyde), 2-methylpropene($C_4H_8$ or isobutene or i-butene), 2-octenal, 2-nonenal, 2-heptenal, 2-hexenal, 2,4-decadienal, 2,4-nonadienal, methyl 2,3-dihydroindene ($C_{10}H_{12}$), dimethylnaphthalene ($C_{12}H_{12}$), alkylbenzene ($C_{15}H_{24}$), n-propylheptane ($C_{10}H_{22}$), n-octadecane ($C_{18}H_{38}$), n-nonadecane ($C_{19}H_{40}$), hexadiene ($C_6H_{10}$), cresol ($C_7H_8O$), sabinene ($C_{10}H_{16}$), methyl heptanol ($C_8H_{18}O$), methyl ethyl pentanol ($C_8H_{18}O$), trimethylpentanol ($C_8H_{18}O$ or ethylhexanol or isooctanol), decanol ($C_{10}H_{22}O$), dodecanol ($C_{12}H_{26}O$), and alkyl dioxolane ($C_6H_{12}O_2$).

21. The method of claim 10 wherein the markers are selected to measure the effect of an increase of free radicals over a normal level wherein the increase of free radicals is related to the disease or other medical condition.

22. Apparatus for detecting the condition of an entity comprising:

a volatile marker detector for non-invasively detecting a set of markers which are characteristic of a condition and which will be found in a gaseous emanation from the entity;

an artificial neural network for processing detected volatile marker data and including fuzzy filters associated with at least one of the input layer and a hidden layer of the artificial neural network.

23. The apparatus of claim 22 wherein the volatile marker detector is an artificial olfactory system.

24. The apparatus of claim 23 wherein the artificial neural network includes an algorithm adapted to the individual entity.

25. The apparatus of claim 22 wherein the volatile marker detector is positioned in or connected to a microwave oven.

26. The apparatus of claim 22 further comprising a heater operatively connected to the volatile marker detector to refresh the detector.

27. The apparatus of claim 26 wherein the detector comprises an array of sensors, and the heater is connected to either the array or to individual sensors.

28. The apparatus of claim 22 wherein the artificial neural network comprises an input layer, an output layer and at least two hidden layers between the input and output layers, each layer comprising a plurality of nodes, wherein the nodes of at least the second hidden layer comprise fuzzy filters.

29. The method of claim 5 wherein the volatile markers are characteristic of *E. Coli, H. Pylori, Salmonella, Staphylococcus aureus,* or *Bacillus anthracis.*

* * * * *